(12) United States Patent　　(10) Patent No.: US 9,987,171 B2
Nandrea et al.　　(45) Date of Patent: Jun. 5, 2018

(54) ABSORBENT ARTICLES HAVING A SENSATION ASPECT

(75) Inventors: Jennifer Joan Nandrea, Cincinnati, OH (US); Masaharu Nishikawa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1590 days.

(21) Appl. No.: 13/033,014

(22) Filed: Feb. 23, 2011

(65) Prior Publication Data

US 2011/0144606 A1　Jun. 16, 2011

Related U.S. Application Data

(63) Continuation of application No. 11/522,668, filed on Sep. 18, 2006, now Pat. No. 7,910,797.

(51) Int. Cl.
| | |
|---|---|
| A61F 7/00 | (2006.01) |
| A61F 13/42 | (2006.01) |
| A61F 13/505 | (2006.01) |
| A61F 13/15 | (2006.01) |
| A61F 13/20 | (2006.01) |
| A61F 5/48 | (2006.01) |
| H01H 85/00 | (2006.01) |

(52) U.S. Cl.
CPC .............. *A61F 13/42* (2013.01); *A61F 13/505* (2013.01)

(58) Field of Classification Search
CPC .. A61F 7/00; A61F 13/15; A61F 13/20; A61F 5/48; H01H 85/00
USPC ................... 604/291, 368, 361, 362
See application file for complete search history.

(56) References Cited

U.S. PATENT DOCUMENTS

| | | |
|---|---|---|
| 3,860,003 A | 1/1975 | Buell |
| 3,929,135 A | 12/1975 | Thompson |
| 4,342,314 A | 8/1982 | Radel et al. |
| 4,463,045 A | 7/1984 | Ahr et al. |
| 4,892,536 A | 1/1990 | Desmarais et al. |
| 4,990,147 A | 2/1991 | Freeland |
| 5,037,416 A | 8/1991 | Allen et al. |
| 5,137,537 A | 8/1992 | Herron et al. |
| 5,151,092 A | 9/1992 | Buell et al. |
| 5,269,775 A | 12/1993 | Freeland et al. |
| 5,649,914 A | 7/1997 | Glaug et al. |
| 5,681,298 A | 10/1997 | Brunner et al. |
| 5,800,416 A | 9/1998 | Seger et al. |
| 5,846,231 A | 12/1998 | Fujioka et al. |
| 6,149,638 A | 11/2000 | Vogt et al. |
| 6,428,526 B1 | 8/2002 | Heindel et al. |
| 6,482,191 B1 | 11/2002 | Roe et al. |
| 6,627,786 B2 | 9/2003 | Roe et al. |
| 6,635,797 B2 | 10/2003 | Olson et al. |

(Continued)

OTHER PUBLICATIONS

All Office Actions, U.S. Appl. No. 11/522,668.

*Primary Examiner* — Michele M Kidwell
*Assistant Examiner* — Ilya Treyger
(74) *Attorney, Agent, or Firm* — Charles R. Matson

(57) ABSTRACT

An absorbent article includes a backsheet having a longitudinal axis, a topsheet attached to the backsheet and having a body-facing surface, and an absorbent core disposed between the backsheet and the topsheet. The article may also include barrier leg cuffs. The article further includes a sensation aspect, which sensation aspect may be provided between the core and the topsheet. The sensation aspect may be, for example, a temperature sensation aspect. A visible indicator may be associated with the sensation aspect.

18 Claims, 17 Drawing Sheets

(56) References Cited

U.S. PATENT DOCUMENTS

| | | |
|---|---|---|
| 6,642,427 B2 | 11/2003 | Roe et al. |
| 6,870,479 B2 | 3/2005 | Gabriel |
| 2003/0060794 A1 | 3/2003 | Olson |
| 2003/0114806 A1 | 6/2003 | LaFortune |
| 2003/0147941 A1 | 8/2003 | Koenig et al. |
| 2004/0254549 A1 | 12/2004 | Olson et al. |
| 2004/0254550 A1 | 12/2004 | Huang et al. |
| 2005/0096612 A1 | 5/2005 | Davis et al. |
| 2005/0222546 A1 | 10/2005 | Vargo et al. |
| 2005/0228349 A1 | 10/2005 | Long et al. |
| 2006/0142714 A1 | 6/2006 | Jackson et al. |
| 2006/0224132 A1 | 10/2006 | Roe et al. |
| 2006/0247588 A1 | 11/2006 | Olson et al. |
| 2007/0048345 A1 | 3/2007 | Huang et al. |
| 2007/0083173 A1 | 4/2007 | Olson |
| 2008/0045913 A1 | 2/2008 | Johnson et al. |
| 2008/0082062 A1 | 4/2008 | Cohen et al. |
| 2008/0082063 A1 | 4/2008 | Ales et al. |
| 2008/0085290 A1 | 4/2008 | Flugge-Berendes et al. |
| 2008/0140165 A1 | 6/2008 | Cohen et al. |
| 2008/0269703 A1 | 10/2008 | Collins et al. |
| 2009/0155325 A1 | 6/2009 | Wenzel et al. |
| 2009/0157025 A1 | 6/2009 | Song et al. |
| 2010/0152689 A1 | 6/2010 | Long et al. |
| 2011/0144602 A1 | 6/2011 | Long et al. |
| 2011/0152806 A1 | 6/2011 | Zhou et al. |
| 2011/0152816 A1 | 6/2011 | Zhou et al. |
| 2012/0264094 A1 | 10/2012 | MacDonald et al. |
| 2013/0034719 A1 | 2/2013 | Zhou et al. |
| 2013/0240139 A1 | 9/2013 | Zhou et al. |
| 2014/0128827 A1 | 5/2014 | Song |
| 2016/0235601 A1 | 8/2016 | Zhou et al. |

ABSORBENT ARTICLES HAVING A SENSATION ASPECT

CROSS REFERENCE TO RELATED APPLICATION

This application is a continuation of U.S. application Ser. No. 11/522,668, filed Sep. 18, 2006 now U.S. Pat. No. 7,910,797, which is hereby incorporated by reference.

FIELD OF THE INVENTION

This invention relates generally to absorbent articles, and more specifically to absorbent articles including a sensation aspect that conveys a signal when wet.

BACKGROUND OF THE INVENTION

Absorbent articles typically have an absorbent assembly held or positioned in proximity to the body of a wearer during use in order to capture and absorb bodily exudates discharged from the wearer. Typical absorbent articles include a topsheet facing the wearer, which permits fluid exudates to pass through, and a backsheet, which prevents the exudates from escaping from the absorbent article. An absorbent core is provided between the topsheet and a backsheet. Frequently, an acquisition layer is provided between the core and the topsheet. Thus, the topsheet permits fluid exudates to pass through, the acquisition layer distributes the exudates to the core such that the exudates are more evenly absorbed, the core absorbs the exudates, and the backsheet prevents the exudates from escaping from the absorbent article.

Disposable absorbent articles such as diapers are designed to absorb and contain bodily waste in order to prevent soiling of the body and clothing of the wearer. Disposable diapers typically are available in different sizes to fit a variety of wearers ranging from newborns to toddlers undergoing toilet training. The design of the diaper typically affects performance, such as the ability to absorb and contain bodily waste. The fit of the diaper on the wearer's body is typically affected by, for example, the size of the diaper waist opening, the size of the openings around the thighs, and the length or "pitch" of the diaper.

The toilet training stage may be referred to as the "point of exit" from the diaper product category because toddlers who have successfully completed toilet training typically no longer wear diapers. The age at which children are toilet trained in developed countries has increased steadily over the past several decades, and is now in the range of about 24-48 months. One reason toilet training has become delayed is that significant technical improvements have been made in diaper dryness and comfort. For example, when wearing a typical modern diaper, the child may have dry skin even after one or more occurrences of urination. As a result, the child may feel little or no discomfort, often may not even be aware that he or she has urinated, and has little incentive to use a toilet.

Some parents may have the child wear cotton training pant or cotton underwear during urinary training so the child feels discomfort following urination in his or her "pants." It is believed that such discomfort assists with learning or provides motivation to learn to voluntarily retain urine. Cloth training pants leave the skin wet and, due to their high breathability, promote evaporative cooling of the skin, further enhancing discomfort. The current tradeoff in this approach, however, if that cloth training pants have poor urine containment, often leading to wet clothing and wet surroundings, e.g., carpeting, furniture, etc. Clearly, there is a need to provide a training signal to the child undergoing urinary toilet training while preventing urine leakage and unnecessary changes of clothing.

Thus, it would be desirable to provide an article that can facilitate urinary toilet training by enhancing a wearer's awareness that urination has occurred, while at the same time providing the protection of an absorbent article to prevent soiling of the wearer's clothing and surroundings. It would be particularly desirable to provide such an article in a form that also provides an effective signal of urination by ensuring that the wearer feels an uncomfortable sensation resulting from urination.

SUMMARY OF THE INVENTION

Absorbent articles, and, more specifically, absorbent articles including a sensation aspect that conveys a signal when wet, are provided. The absorbent article includes a backsheet having a longitudinal axis, a topsheet attached to the backsheet and having a body-facing surface, and an absorbent core disposed between the backsheet and the topsheet. The article further includes a sensation aspect, which may be provided between the core and the topsheet. The sensation aspect may be, for example, a temperature sensation aspect. A visible indicator may be associated with the sensation aspect.

In one embodiment, the absorbent article includes a backsheet having a longitudinal axis, a topsheet having a body-facing surface, an absorbent core disposed between the backsheet and the topsheet, and a temperature sensation aspect that produces a change in temperature when wet and includes a carrier layer. The temperature sensation aspect is provided between the core and the topsheet. The position of the temperature sensation aspect on the core correlates to a sensation aspect position of the core. The sensation aspect position on the core absorbs less urine than surrounding areas of the core.

In another embodiment, the absorbent article includes a backsheet having a longitudinal axis, a topsheet having a body-facing surface, an absorbent core disposed between the backsheet and the topsheet, and a temperature sensation aspect that produces a change in temperature when wet and includes a carrier layer. The temperature sensation aspect is provided between the core and the topsheet. The temperature sensation aspect is configured for increased urine flow therethrough.

In a further embodiment, the absorbent article includes a backsheet having a longitudinal axis, a topsheet having a body-facing surface, an absorbent core disposed between the backsheet and the topsheet, and a temperature sensation aspect that produces a change in temperature when wet and includes a carrier layer. The temperature sensation aspect is configured to enhance contact of the temperature sensation agent with skin of a wearer.

In yet another embodiment, the absorbent article includes a backsheet having a longitudinal axis, a topsheet having a body-facing surface, an absorbent core disposed between the backsheet and the topsheet, and a temperature sensation aspect that produces a change in temperature when wet and includes a carrier layer. The temperature sensation aspect is provided between the core and the topsheet. The sensation aspect comprises a top surface and a bottom surface and wherein one of the top surface or the bottom surface comprises a frictional coupling mechanism.

In yet a further embodiment, the absorbent article includes a backsheet having a longitudinal axis, a topsheet having a body-facing surface, an absorbent core disposed between the backsheet and the topsheet, and a temperature sensation aspect that produces a change in temperature when wet and includes a carrier layer. The temperature sensation aspect is provided between the core and the topsheet. The temperature sensation aspect includes a graphic indicator for indicating placement or action of the sensation aspect.

Additional aspects of the disclosure are defined by the claims of this patent. While multiple embodiments are disclosed herein, still other embodiments of the invention will become apparent to those skilled in the art from the following detailed description, which shows and describes illustrative embodiments of the invention. As will be realized, the invention is capable of modifications in various obvious aspects, all without departing from the spirit and scope of the invention. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Absorbent articles, and more specifically, absorbent articles including a sensation aspect that conveys a signal when wet, are provided. The term "absorbent article" refers to a device that absorbs and contains liquid, and more specifically, refers to a device that is placed against or in proximity to the body of the wearer to absorb and contain the various exudates discharged from the body. The discussion herein focuses on disposable absorbent articles such as diapers having a sensation aspect. However, the sensation aspect may be applied to any absorbent articles. In the discussion below of the Figures, elements common to all embodiments are numbered similarly in all Figures, while those elements unique to each embodiment are numbered differently.

Diapers having a sensation aspect are currently available. Such diapers include a uniformly sized "cool patch" (approximately 3"×3") located in the crotch region of the diaper between the core and the top sheet, all described more fully below. The cool patch emits a cool sensation when wet. If the cool patch is in contact with the wearer, the cool patch thus makes the wearer aware of soiling through the cool sensation. While these diapers provide a sensation aspect, the cool patch frequently does not have adequate skin contact to convey an alarm to the wearer. The cool patch may interfere with absorbency of the diaper in the region of the cool patch, thus interfering with the primary utility of the diaper. The present invention addresses these and other problems associated with diapers having a sensation aspect that are currently available.

Figure 1:
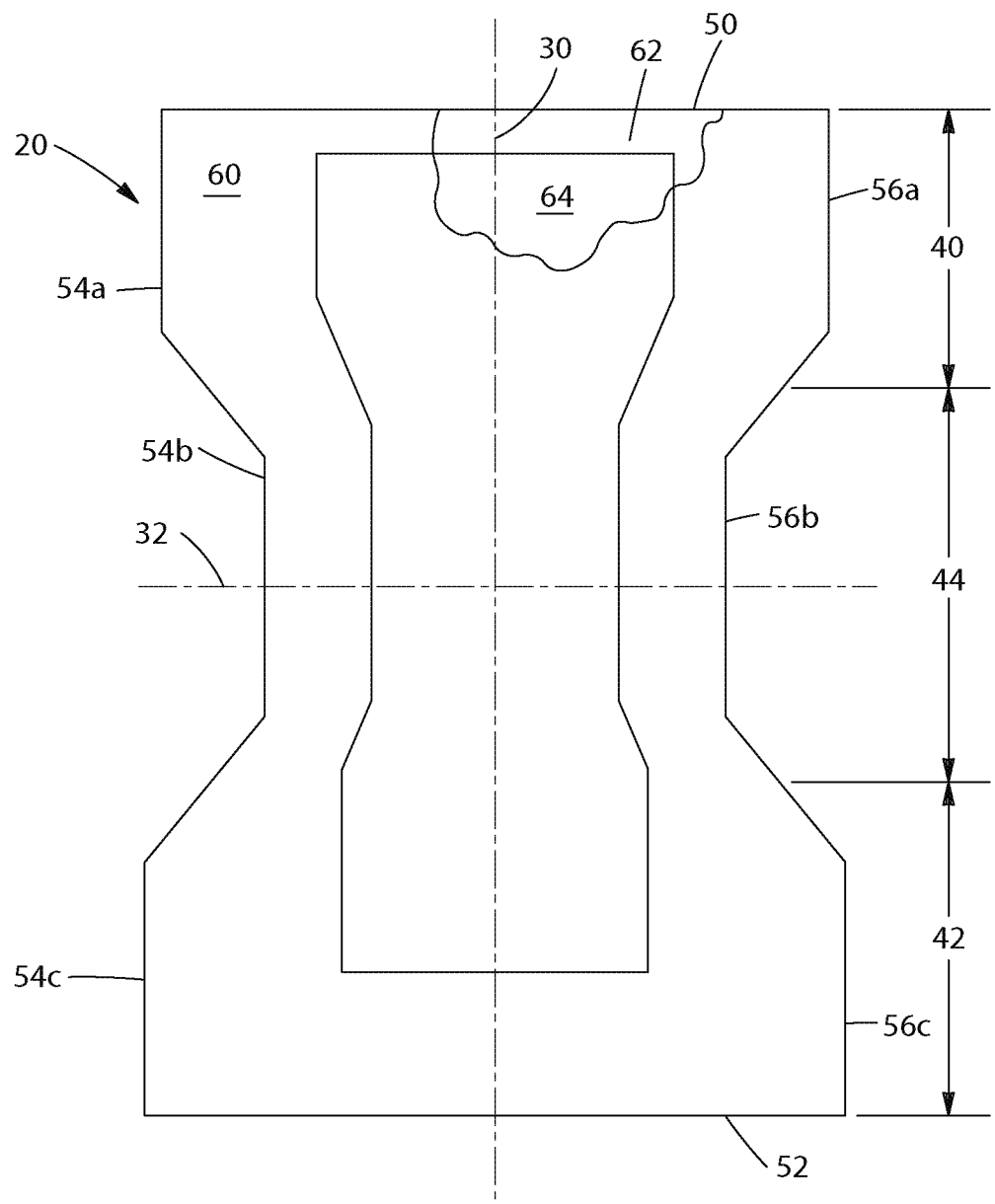
FIG. 1 illustrates a disposable absorbent article in a flat orientation.

FIG. 1 is a plan view of an exemplary disposable absorbent article 20 in its flat, uncontracted state, i.e., without elastic-induced contraction. Portions of the article 20 have been cut away to more clearly show the underlying structure of the disposable absorbent article 20. As illustrated, the portion of the disposable absorbent article 20 that contacts the wearer faces the viewer (i.e., showing the interior or inner side of the article). The disposable absorbent article 20 has a longitudinal axis 30 and a transverse axis 32.

One end portion of the disposable absorbent article 20 is configured as a first waist region 40 of the disposable absorbent article 20. The opposite end portion is configured as a second waist region 42 of the disposable absorbent article 20. The waist regions 40 and 42 generally comprise those portions of the disposable absorbent article 20 that, when worn, encircle the waist of the wearer. The waist regions 40 and 42 may include elastic elements, which gather about the waist of the wearer to provide improved fit and containment. An intermediate portion of the disposable absorbent article 20 is configured as a crotch region 44, which extends longitudinally between the first and second waist regions 40 and 42. The crotch region 44 is that portion of the disposable absorbent article 20 that, when the disposable absorbent article 20 is worn, is generally positioned between the legs of the wearer.

The disposable absorbent article 20 has a laterally extending first waist edge 50 in the first waist region 40 and a longitudinally opposing and laterally extending second waist edge 52 in the second waist region 42. The disposable absorbent article 20 has a first side edge 54 and a laterally opposing second side edge 56, both side edges extending longitudinally between the first waist edge 50 and the second waist edge 52. The portion of the first side edge 54 in the first waist region 40 is designated 54a, the portion in the crotch region 44 is designated 54b, and the portion in the second waist region 42 is designated 54c. The corresponding portions of the second side edge 56 are designated 56a, 56b, and 56c, respectively.

The disposable absorbent article 20 comprises a water-permeable topsheet 60, a water-impermeable backsheet 62, and an absorbent assembly or core 64, which may be disposed between the topsheet 60 and the backsheet 62 with the topsheet 60 attached to the backsheet 62. The topsheet 60 may be fully or partially elasticized, or it may be foreshortened so as to provide a void space between the topsheet 60 and the core 64. Exemplary structures including elasticized or foreshortened topsheets are described in greater detail in U.S. Pat. Nos. 4,892,536, 4,990,147, 5,037,416, and 5,269,775, among others.

Figure 2:
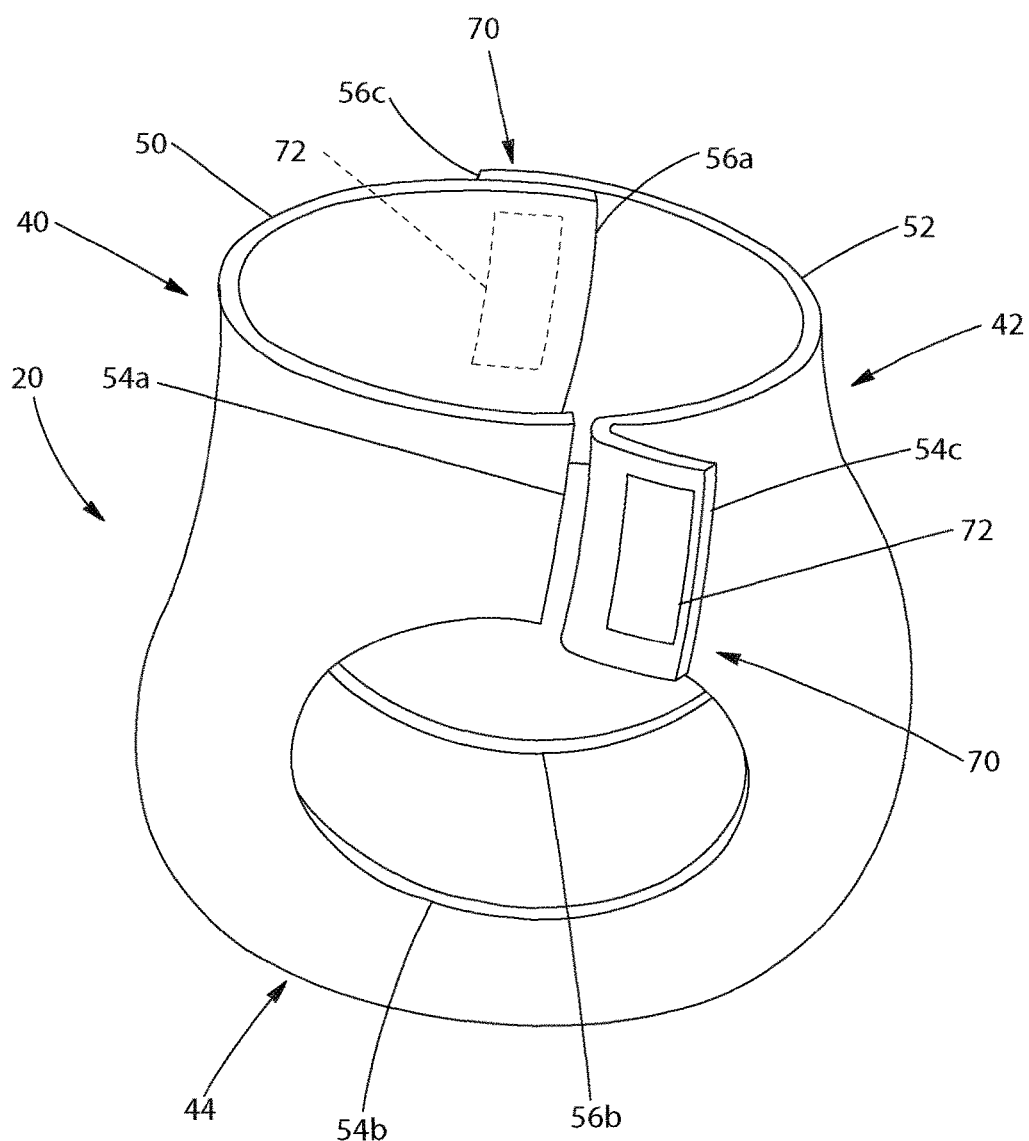
FIG. 2 illustrates a disposable absorbent article as it would be worn.

FIG. 2 illustrates the article illustrated in FIG. 1 configured as it would be worn. The disposable absorbent article 20 may be sealed at the sides so as to be configured as illustrated in FIG. 2. However, the article 20 may instead include refastenable side seams 70 that can be used to fasten the waist regions 40, 42 together. According to one embodiment, the waist regions 40, 42 may be fastened at the sides to apply the article like a diaper. According to a further embodiment, illustrated in FIG. 2, the side seams 70 may include fasteners 72 that can be used to configure the article like a pair of pull-on training pants or disposable pants. Any suitable side seams may be used. The side seams may be detachable, permanent, tearable, or combinations of the above.

As illustrated, the fasteners 72 may be disposed on the interior of the disposable absorbent article 20 in the second waist region 42 adjacent to the portion 54c of the first side edge 54 and adjacent to the portion 56c of the second side edge 56. The portion 54c of the side edge 54 is shown in an open condition, such as prior to closing and fastening or after being reopened. In alternative embodiments, the fasteners 72 may not be configured for closing and reopening. The portion 56c of the opposing side edge 56 as shown in FIG. 2 is fastened, i.e., forming a pants configuration. In FIG. 2, the second waist region 42 overlaps the first waist region 40 when they are fastened together.

The fasteners 72 may be formed of any material and in any form that will releasably attach to the mating surface of the opposing waist region when pressed against it. For example, the primary fastening component may be a mechanical fastener that releasably engages with the mating surface, such as by means of a plurality of hooks engaging with loops formed by fibers in a nonwoven sheet. Alternatively, the primary fastening component may be an adhesive that releasably adheres to the mating surface.

Still other variations are also possible. For example, the fasteners 72 may be disposed on the interior of the article 20 in the first waist region 40 such that the first waist region 40 overlaps the second waist region 42 when they are fastened together. As another example, the fasteners 70 may be disposed on the exterior of the article 20 rather than on the interior. As a further example, the fasteners 70 may be used with a specific mating fastener surface particularly suited for cooperation with the fasteners 70 (e.g., a loop layer that works with a hook fastener, or a layer particularly treated to provide a suitable contacting surface for a specific adhesive). Additional exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428,526, among others.

Figure 3:
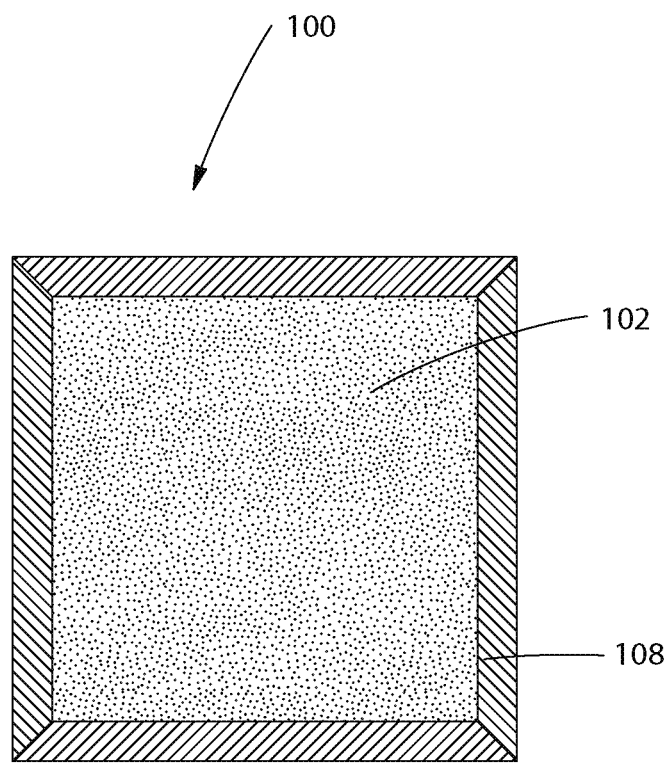
FIG. 3 illustrates a top view of sensation aspect.
Figure 4:
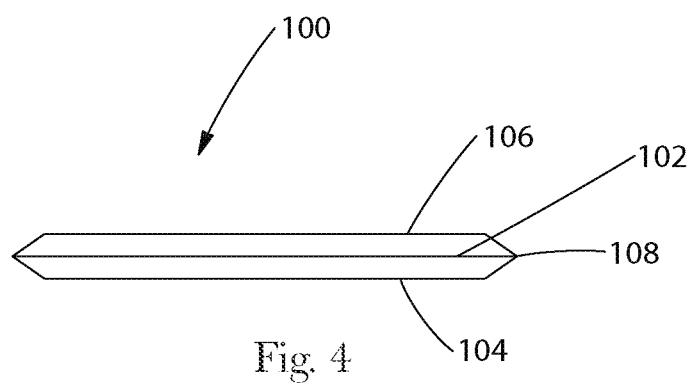
FIG. 4 illustrates a side view of a sensation aspect.
Figure 5:
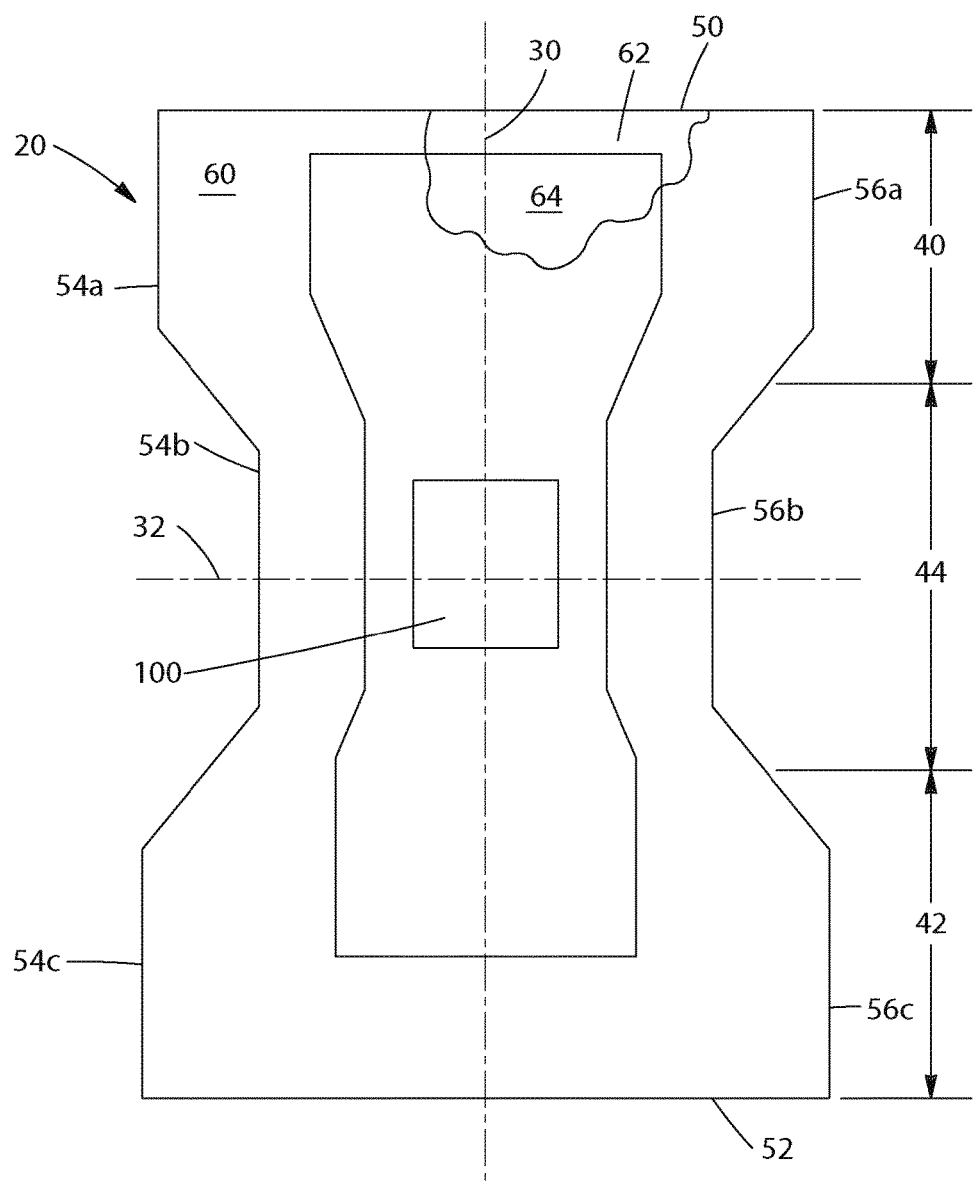
FIG. 5 illustrates a disposable absorbent article having a sensation aspect.

As shown in FIGS. 3, 4, and 5, the disposable absorbent article 20 may be combined with or assembled to include a sensation aspect 100. FIGS. 3 and 4 illustrate a sensation aspect such as may be provided on a diaper. FIG. 3 illustrates a top view and FIG. 4 illustrates a side view of the sensation aspect. FIG. 5 shows the disposable absorbent article 20, such as is illustrated in FIGS. 1 and 2, combined with or assembled to include a sensation aspect 100. While the absorbent articles illustrated include a single sensation aspect, the articles may include a plurality of sensation aspects according to other embodiments.

The sensation aspect 100 illustrated is a structure that is formed separately from, but discretely attached to, the inner portion of the article 20. The sensation aspect 100 may be positioned between the core 64 and the topsheet 60. The sensation aspect 100 includes a temperature sensation agent 102. The temperature sensation agent may be a composition or structure. In the embodiment shown, the temperatures sensation agent 102 comprises sorbitol crystals. When contacted with urine, the sorbitol crystals dissolve and undergo an endothermic reaction, thus emitting a cold sensation. The sensation aspect 100 comprises a carrier layer 104 for supporting the sensation agent 102. Further, a trapping layer 106 may be provided for maintaining the temperature sensation agent 102 in place. A seam 108 may be provided between the carrier layer 104 and the trapping layer 106. The seam may comprise heat sealing, an adhesive, or any other manner of coupling the carrier layer 104 to the trapping layer 106. Generally, as discussed in relation to FIG. 5, the temperature sensation agent 102 may be disposed on the surface of the carrier layer 104 closer to the wearer's skin (i.e., body-facing surface).

It will be recognized that the temperature sensation agent may include those materials that produce a temperature change (i.e., involve an endothermic or an exothermic reaction), as well as those that produce the sensation that a temperature change has occurred without actually producing a temperature change. For example, the temperature sensation agent may be a cooling agent. In one embodiment, the cooling agent comprises sorbitol crystals. In alternative embodiments, the cooling agent may be a dye, such as AQUACOOL dye manufactured by United Polymer Technology of Akron, Ohio. The AQUACOOL dye is a water-soluble dye that changes temperatures when brought into contact with water. Another example of cooling agent may be menthol or a menthol derivative, which chemicals are believed to provide the sensation of a temperature change, while not actually producing a temperature change. The COOLACT P and COOLACT 10 products manufactured by LIPO Chemicals of Paterson, N.J. are examples of menthol derivative products that may be suitable. Other examples of temperature change agents (e.g., endothermic salts) that may be suitable temperature sensation agents may be found in U.S. Pat. No. 6,642,427.

FIG. 5 illustrates a standard disposable absorbent article or diaper configuration, such as shown in FIG. 1, having a sensation aspect, such as shown in FIGS. 3 and 4. As shown, the diaper 20 includes a topsheet 60, a core 64, and a backsheet 62. The topsheet 60 has a body-facing surface (on top as viewed in FIG. 5), and permits fluid exudates to pass through. The core 64 absorbs the exudates, and the backsheet 62 prevents the exudates from escaping from the absorbent article 20. A sensation aspect 100 is provided generally at the crotch region 44 between the core 64 and the topsheet 60. The sensation aspect 100 may be, for example, a cooling patch. As discussed with respect to FIGS. 3 and 4, such cooling patch is formed of a carrier layer 104 and a temperature sensation agent 102. The temperature sensation agent 102 undergoes an endothermic reaction when contacted by urine, thus emitting a temperature sensation. In one embodiment, the temperature sensation is a cool sensation. In the embodiment shown, the temperature sensation aspect is sized approximately 3 inches by 3 inches. An adhesive layer may be provided between the core and the sensation aspect and/or between the sensation aspect and the top sheet.

In addition to the features described above, the disposable absorbent article 20 may also include a variety of features known in the art, such as slit openings, outer leg cuffs, front and rear panels, waist cap features, elastics, and the like to provide desired fit, containment, and aesthetic characteristics. Such additional features are described in U.S. Pat. Nos. 3,860,003, 5,151,092, and 6,482,191, among others. Additionally, a transfer layer, which also may be referred to as an acquisition or distribution layer, may be disposed between the topsheet 60 and the core 64. In the embodiment of FIG. 5, the acquisition layer thus is disposed between the topsheet 60 and the sensation aspect 100. Moreover, the elements discussed above may be modified from their illustrated forms.

FIGS. 6-16 illustrate embodiments of diapers having a sensation aspect, wherein the sensation aspect comprises a temperature sensation patch, the temperature sensation patch having improved temperature sensation, the sensation aspect having increased travel capacity of urine, and/or the diaper having improved containment. The sensation aspect includes a carrier layer 104 having a body-facing surface and an opposite surface facing toward the core 64, and an active component 102 on one of the body-facing surface or the opposite surface of the sensation aspect. Unless otherwise described, the active component 102 is provided on the body-facing surface of the carrier layer 104.

In use, the crotch region 44 of the diaper 20 tends to sag away from the wearer. In diapers having a sensation aspect 100 that are currently available, the sensation aspect 100 is provided at the crotch region 44, approximately adjacent the core 64. Thus, there is little vertical distance between the core 64 and the sensation aspect 100. Because of both the placement of the sensation aspect 100 on the diaper 20 and the vertical placement of the sensation aspect 100 on the diaper layers (including topsheet 60, the core 64, and the backsheet 62), the efficacy of the sensation aspect 100 in communicating an alarm sensation such as a cool sensation to the wearer may be compromised.

As discussed above, diapers with sensation aspects that are currently available have the sensation aspect positioned between the core and the topsheet. The sensation aspect is kept in place via an adhesive layer over substantially all of its bottom surface and an adhesive layer over substantially all of its top surface. Thus, the adhesive layer on the top surface couples the sensation aspect to the topsheet. The adhesive layer on the bottom surface couples the sensation aspect to the core, either directly or indirectly via a transfer or acquisition layer. An adhesive layer over substantially all of the top surface negatively affects the proximity of the sensation aspect to the wearer's skin. An adhesive layer over substantially all of the bottom surface can impact floating performance.

Figure 6:
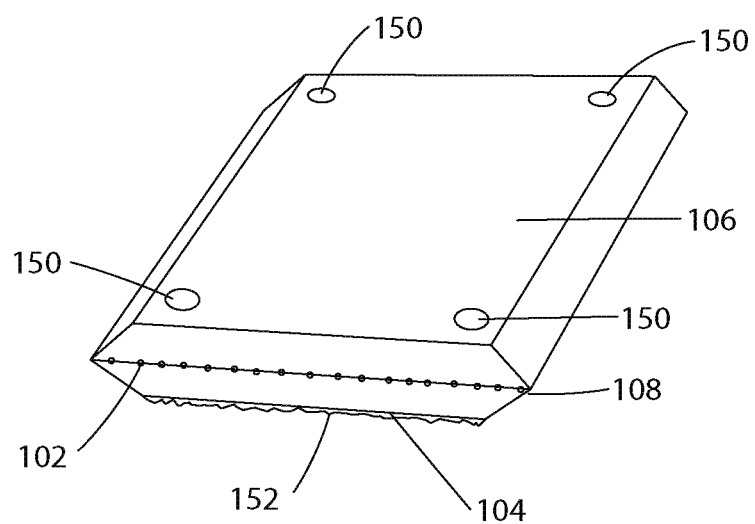
FIG. 6 illustrates a sensation aspect having a top surface with a first coupling mechanism and a bottom surface with a second coupling mechanism in accordance with one embodiment of the present invention.

FIG. 6 illustrates a first coupling mechanism along the top surface of the sensation aspect and a second coupling mechanism along the bottom surface of the sensation aspect. The first coupling mechanism is one or more regions 150 on the top surface provided with an adhesive, which may cover any or no portion of the top surface. As shown, the top surface is the trapping layer 106. As discussed herein, the top surface may alternatively be the surface having the sensation agent 102 or another surface. Each adhesive region 150 may be substantially less than the entire top surface. In the embodiment of FIG. 6, four adhesive regions 150, one provided approximately at each corner of the top surface of the sensation aspect 100, are shown. More or fewer adhesive regions 150 may be provided and the location of the adhesive regions 150 may vary. Any suitable adhesive may be used at each adhesive region 150. The adhesive regions 150 may be substantially uniform in appearance with the remaining surface of the sensation aspect 100 or may be visually distinct, for example by coloration. The second coupling mechanism is a frictional coating 152 to enable friction coupling between the sensation aspect 100 and the surface therebeneath (for example, the core or a transfer layer). The frictional coating 152 may be any suitable coating for imparting a friction to the surface of the sensation aspect 100. Each of the regions for the first and second coupling mechanisms may be of any suitable geometry, or no particular geometry at all. Alternatively, the relevant surface of the sensation aspect 100 may itself be configured to have friction against the engaging surface of the absorbent article. Thus, in an alternative embodiment, the bottom surface of the carrier layer 104 may be configured to have friction against the engaging surface of the core or, if provided, the transfer or acquisition layer. In alternative embodiments, the first coupling mechanism may be provided on both the top and the bottom surface, the second coupling mechanism may be provided on both the top and the bottom surface, the second coupling mechanism may be provided on the top surface and the first coupling mechanism may be provided on the bottom surface, one of the first or second coupling mechanism may be provided on either the top or bottom surface with the other surface being provided with no coupling mechanism, no coupling mechanism could be provided on either surface, some of each can be provided on one or more surfaces, or some other combination may be used.

Figure 7:
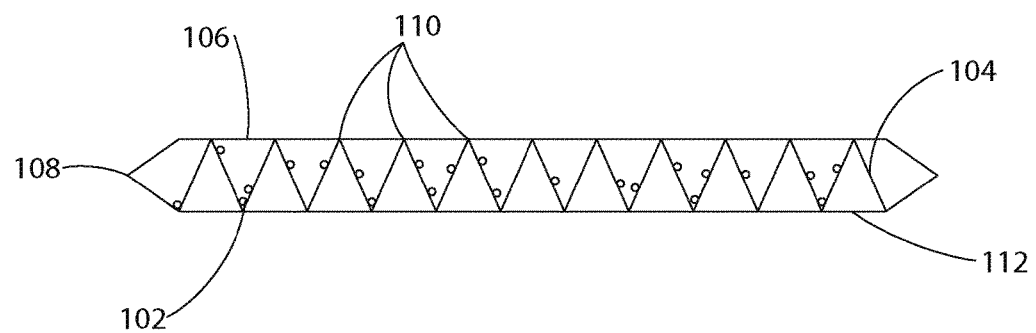
FIG. 7 illustrates a sensation aspect having a folded carrier layer in accordance with one embodiment of the present invention.

FIG. 7 illustrates an embodiment wherein the sensation aspect 100 is provided with three-dimensional shape. The three-dimensional shape provides a larger surface area and raises the height of the sensation aspect 100, thus bringing it in closer contact with the skin of the wearer. In the embodiment of FIG. 7, the sensation aspect 100 comprises folds or creases 110 along the carrier layer 104 to impart a three-dimensional shape. An additional carrier layer 112 may be provided underneath the carrier layer 104 to maintain the folds 110. Alternatively, no additional carrier layer 112 may be provided. In the embodiment shown, the trapping layer 106 is provided in a relatively flat orientation over the folds 110 of the carrier layer 104. Such flat orientation may provide a smoother surface under the topsheet 60, the enhancing comfort for the wearer. In alternative embodiments, both the carrier layer 104 and the trapping layer 106 may comprise folds 110. Other suitable methods of imparting a three-dimensional shape may alternatively be used.

In another alternative embodiment, a structure or a substance may be used to bring the sensation aspect 100 into closer contact with the wearer's skin, thus improving temperature conductivity. This can be done by having a thicker core portion adjacent the sensation aspect 100, by having some other material between the sensation aspect and the core, by using a substance that expands when the user urinates, such as a foaming agent as disclosed in U.S. Published Application No. 2005/0228349, or by any other suitable means.

Generally, the core 64 of the diaper 20 includes absorbent gelling material (AGM) to absorb urine. AGM is a super absorbent polymer and typically has an exothermic reaction exuding heat when contacted with urine. In an embodiment wherein the sensation aspect 100 comprises a cool patch having a temperature sensation agent 102 that undergoes an endothermic reaction, such as sorbitol crystals, the sensation aspect 100 emits a cool sensation, and it is this cool sensation that indicates to the wearer that he or she has urinated. However, as can be expected, urine travels through the sensation aspect 100 to the core 64. Thus, very shortly after the endothermic reaction of the sensation aspect 100 is initiated, the urine contacts the AGM and initiates an exothermic reaction and thus emitting an at least slightly warm sensation. Additionally, urine itself is generally warm. Thus, the exothermic reaction of the AGM, the warm temperature of urine, or both can counterbalance the sensation emitted by the endothermic reaction of the sensation aspect 100.

Figure 8:
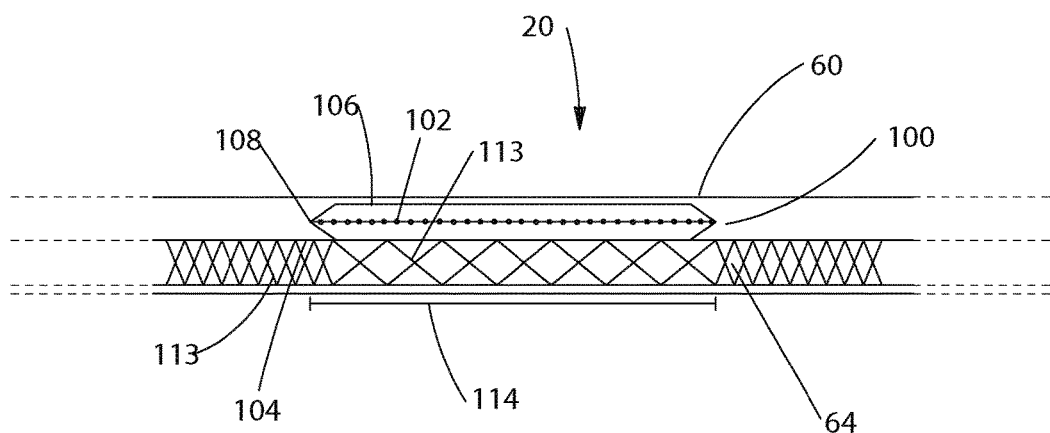
FIG. 8 illustrates a disposable absorbent article having a sensation aspect wherein the core of the disposable absorbent article includes a targeted zone with reduced absorbent capacity in accordance with one embodiment of the present invention.

FIG. 8 illustrates an embodiment to mitigate the effect of the AGM's exothermic reaction on the sensation emitted by the endothermic reaction of the sensation aspect 100. The core 64 thus comprises AGM 113. In the embodiment of FIG. 8, a portion 114 of the core 64 generally corresponding in location to the placement of the sensation aspect 100 has a reduced amount of AGM 113. This can be accomplished either by reducing the amount of AGM 113, resulting in a thinner core, by mixing another material with the AGM 113 at the desired location, other suitable means, or any combination of the above. The portion 114 of the core 42 thus has a reduced absorbent capacity. Stated otherwise, the core 64 includes a targeted zone 114 with reduced absorbent capacity. As a result, the zone 114 has decreased ability for an exothermic reaction.

Figure 9:
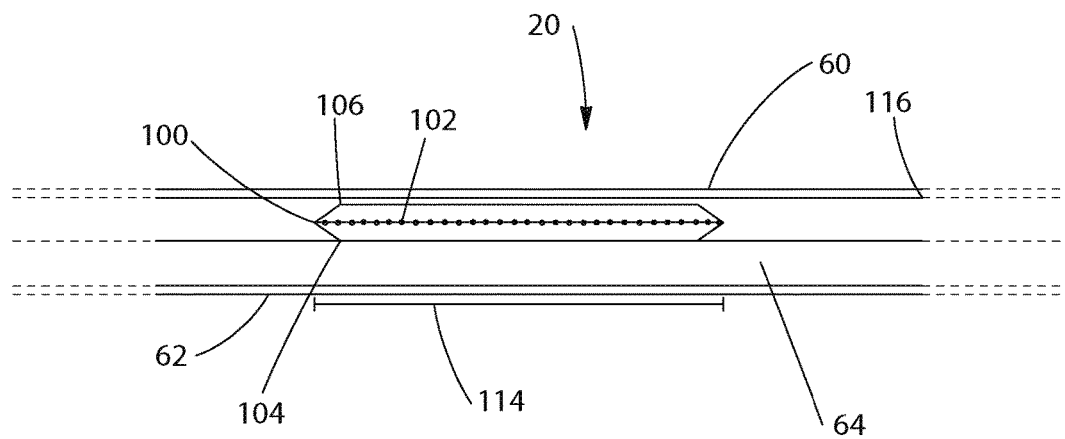
FIG. 9 illustrates a disposable absorbent article having an acquisition layer at a location generally corresponding to the location of a sensation aspect in accordance with one embodiment of the present invention.
Figure 10:
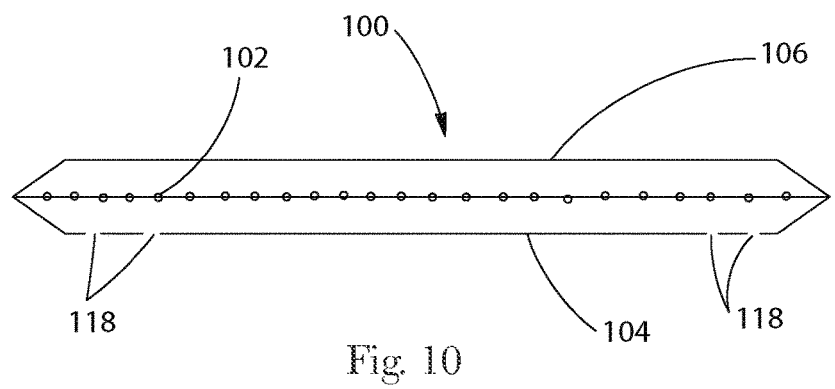
FIG. 10 illustrates a sensation aspect having travel paths for urine flow in accordance with one embodiment of the present invention.

Alternatively, as shown in FIG. 9, an acquisition layer 116 may be provided at least at the portion 114 of the diaper 20 generally corresponding to the location of the sensation aspect 100. The acquisition layer 116 may be disposed above or below the sensation aspect 100, in whole or in part. In one embodiment, an acquisition layer 116 may be disposed above the sensation aspect 100, in whole or in part, and another acquisition layer 116 may be disposed below the sensation aspect 100, in whole or in part. The acquisition layer 116 may be designed to wick urine from the sensation aspect 100 to other areas of the core 64, thus decreasing urine flow to the core 64 at the location generally corresponding to the location of the sensation aspect 100.

In yet a further embodiment, an alternative absorbing agent having no exothermic reaction may be provided in the core at the location generally corresponding to the location of the sensation aspect. Such alternative absorbing agent may be, for example, a fiber. In other embodiments, the AGM 113 may be mixed with, or replaced by, a substance that is cooling or less exothermic than the AGM 113.

Another problem that occurs with diapers having a sensation aspect as currently available is that the sensation aspect may block liquid from traveling uniformly to the core for absorption. The positioning of the sensation aspect 100 on the diaper 20, as shown in FIG. 5, for example, may be determined to allow enough liquid to bypass the sensation aspect 100 to the core 64 so as to enhance liquid flow to the core and prevent flooding. Flooding may result in leakage of the article 20 during urination, which is undesirable in the article 20. Consequently, the dimensions of the sensation aspect 100 may be varied to prevent flooding while at the same time wicking sufficient liquid to exude a sensation, such as a cooling sensation, to the wearer.

Further, flooding may occur when the carrier layer 104 of the sensation aspect 100 is hydrophobic. While the urine may travel through the temperature sensation agent 102, a hydrophobic carrier layer 104 prevents further travel through the sensation aspect 100. Which such blocking may mitigate exothermic reaction by absorption by the AGM of the core, it is generally contrary to the purpose of the diaper: namely, to absorb bodily exudates. In an embodiment for improving travel of urine through the sensation aspect, shown in FIG. 10, the sensation aspect 100 may have travel paths 118 such as slits or holes. As shown, the travel paths 118 may be provided only in the carrier layer 104 of the sensation aspect 100. Alternatively, travel paths 118 may be provided through a trapping layer 106 and the carrier layer 104. Further, as shown, the travel paths 118 may be provided generally along peripheral edges of the sensation aspect 100. Alternatively, the travel paths 118 may be provided generally throughout the sensation aspect 100 or in any configuration desired.

Figure 11:
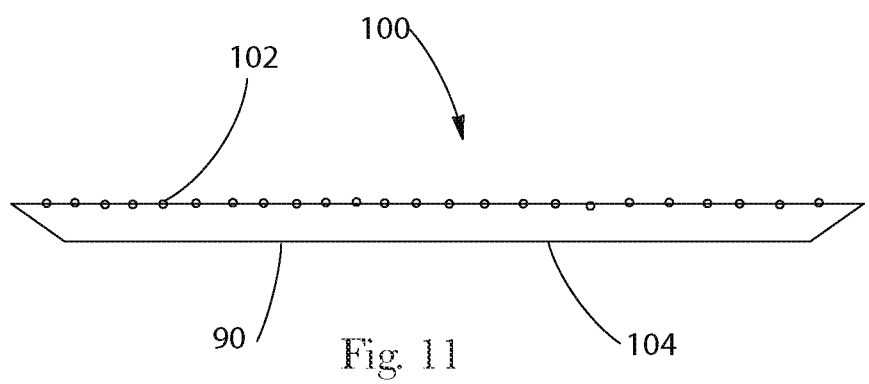
FIG. 11 illustrates a sensation aspect having a hydrophilic coating on a surface farthest from the wearer, the hydrophilic coating covering the entire carrier surface, in accordance with one embodiment of the present invention.
Figure 12:
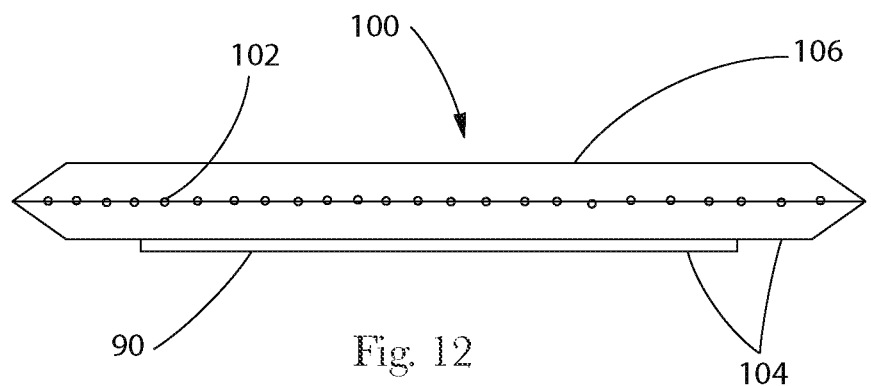
FIG. 12 illustrates a sensation aspect having a hydrophilic coating on a surface farthest from the wearer, the hydrophilic coating covering a portion of the carrier surface, in accordance with one embodiment of the present invention.
Figure 13:
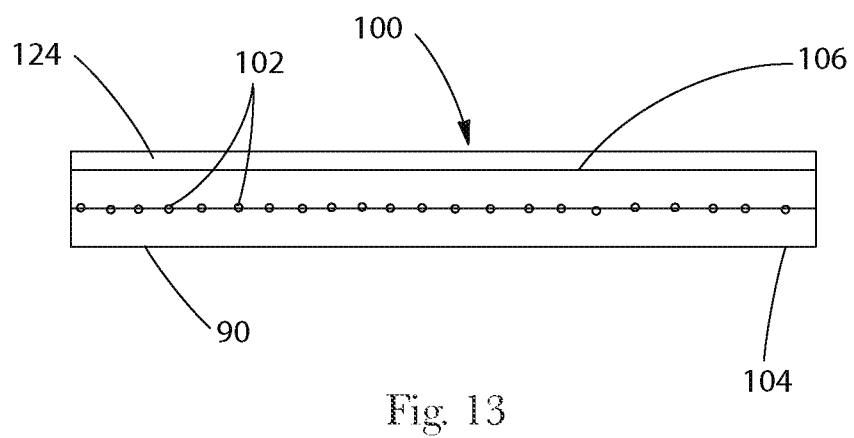
FIG. 13 illustrates a sensation aspect having a three dimensional film on a surface closest to the wearer and a hydrophilic coating on a surface farthest from the wearer, in accordance with one embodiment of the present invention.
Figure 14:
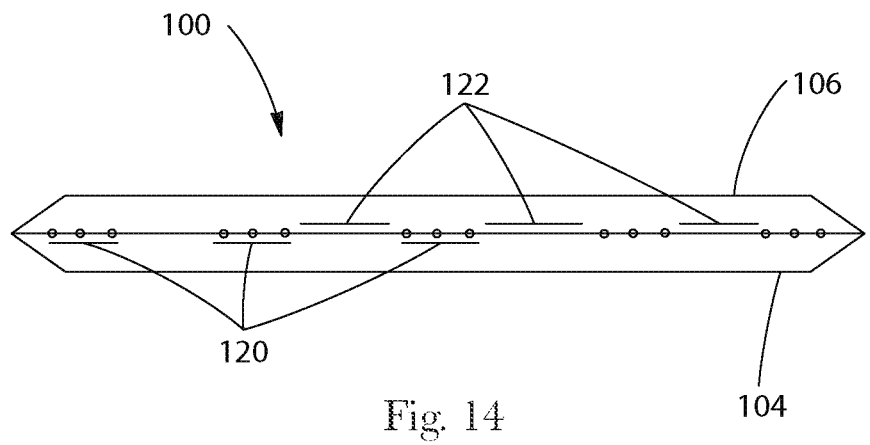
FIG. 14 illustrates a sensation aspect having the temperature sensation agent concentrated in certain areas in accordance with one embodiment of the present invention.

FIGS. 11-13 illustrate embodiments of a sensation aspect 100 comprising a hydrophilic layer 90. These embodiments improve liquid travel through the sensation aspect 100. In alternative embodiments, the carrier layer 104 may comprise the hydrophilic layer 90 in whole, as shown in FIG. 11, or in part, as shown in FIG. 12. The hydrophilic layer 90 may be continuous, discontinuous, in a pattern, or in any suitable configuration. Further, FIG. 12 illustrates a trapping layer 106 while no trapping layer 106 is provided in the embodiments of FIG. 11. In the embodiments of FIGS. 11 and 12, the temperature sensation agent 102 is provided on the surface of the sensation aspect 100 closest to the wearer. Exemplary materials suitable for use in the hydrophilic layer 90 include nonwovens, foams, woven materials, etc. In particular, the hydrophilic layer 90 may comprise, by way of illustration and not limitation, rayon, Lyocell and other cellulose-based materials, cotton, polyester, polypropylene and polypropylene blends (e.g., with other listed materials, such as a Lyocell/polypropylene blend), and hydrophilic forms of nonwovens such as SM (spunbond meltblown), SMS (spunbond meltblown spunbond), and SMMS (spunbond meltblown meltblown spunbond). It will be also recognized that the hydrophilic coating may include a diverse range of materials, including lotions, creams and the like. Exemplary hydrophilic coatings include surfactants, such as the NUWET silicone surfactant available from GE Silicones of Wilton, Conn.

In the embodiments of FIGS. 11 and 12, a temperature sensation agent 102 is provided. While the temperature sensation agent 102 is shown spaced from the carrier layer 104 for the purposes of illustration, it is to be appreciated that the temperature sensation agent 102 may be provided adjacent the carrier layer 104. The temperature sensation agent 102 provides a sensation of temperature change, for example, of a cool temperature upon contact with urine. In addition to the sensation of cool temperature, a sensation of wetness may be provided via the hydrophilic layer 90. Thus, the hydrophilic layer 90 acts to maintain the feeling of wetness to the wearer.

Moreover, according to a further variation shown in FIG. 13, the sensation aspect 100 may comprise three dimensional film 124. The three dimensional film 124 may be provided over the trapping layer 106.

Further, the hydrophilic coating or layer 90, the three dimensional film 124, and temperature sensation agents 102 described above may be used with other sensation aspects. Moreover, the coatings and agents may be useful in conjunction with the structures described in U.S. Pat. No. 6,627,786, among others.

In some embodiments, the carrier layer 104 may be hydrophobic or hydrophilic but liquid flow through the sensation aspect 100 may be compromised because of the temperature sensation agent 102 within the sensation aspect 100. In one embodiment for improving travel of urine through the sensation aspect 100, the sensation aspect 100 may have a reduced density of temperature sensation agent 102, thus increasing the liquid flow through the sensation aspect 100 and thus to the core 64. In the embodiment shown in FIG. 14, the cooling ingredient 102 is concentrated in certain areas 120 on the sensation aspect 100. The concentration may be in a linear fashion, or in any other suitable manner. Thus, for example, alternating linear areas 122 having no temperature sensation agent 102 are provided on the sensation aspect 100. The alternating linear areas 122 having no temperature sensation agent 102 are thus suited for liquid flow assuming a hydrophobic or hydrophilic carrier layer 104.

Thus, during insults of urine, in accordance with various embodiments described herein, urine is able to penetrate in the z-direction and a medium for the flow of urine may be enabled in the x-y plane via wicking. A hydrophilic layer or coating 90, travel passages 118, alternating linear areas 122 having no temperature sensation agent 102, or other devices or configurations may be provided to enhance the movement of the urine in the z-direction and/or in the x-y plane. Enhancement of movement of urine in the x-y plane, for example via a hydrophilic layer 90 or acquisition layer 116, both previously discussed, expands the wetted area of the sensation aspect, which preferably is held in contact with the wearer's skin. The wicking in the x-y plane causes the urine to spread out and effectively wet a large area before being absorbed into the core 64, thereby maximizing the wetness signal experienced by the wearer.

The sensation aspect 100 may have a high initial wetness that dries out after, for example, approximately 10 minutes. That is, while the initial wetness may vary, in one embodiment, the sensation aspect 100 may be designed to provide period of initial wetness to cause the wearer to recognize the condition, and the wetness over time to be limited so as not to create, for example, skin health issues because of too much wetness being present near the skin over a prolonged period of time.

Figure 15:
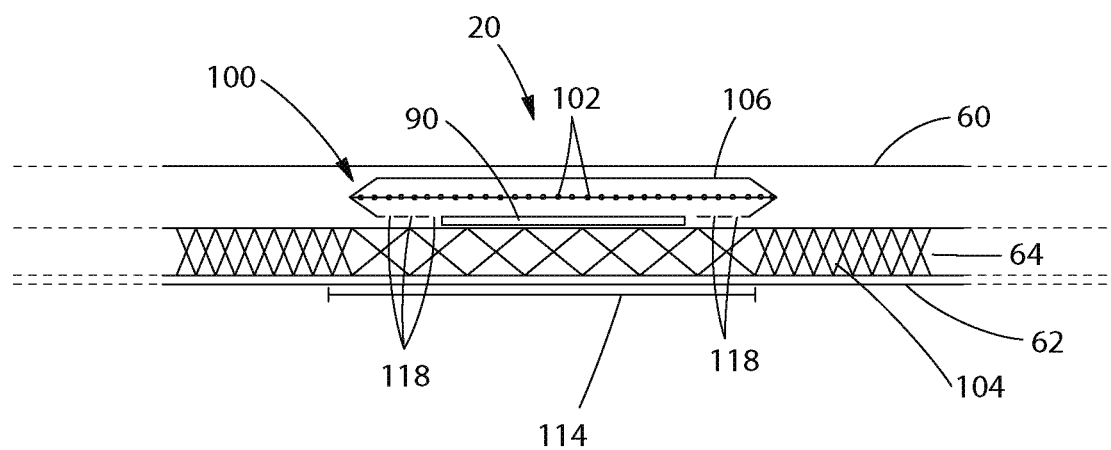
FIG. 15 illustrates a disposable absorbent article including a sensation aspect having travel paths for urine flow, a hydrophilic coating, and targeted reduced absorbent capacity in the core.

In accordance with a further embodiment, as shown in FIG. 15, the diaper may be combinations of aspects described above. Thus, as shown, the diaper 20 includes a sensation aspect 100 having increased liquid flow through the sensation aspect via travel paths 118 in the carrier layer 104, has a hydrophilic coating 90 on the carrier layer 104 for increased urine flow in the x-y plane, and has targeted reduced absorbent capacity in the core 64 at a location 114 generally corresponding to the location of the sensation aspect 100.

With specific reference to diapers having a sensation aspect comprising a cool patch having sorbitol crystals, when the cool patch becomes wet, the dissolved sorbitol crystals become somewhat viscous or slimy to the touch. FIG. 113 illustrates an embodiment for minimizing the slimy feel. As shown, three-dimensional film 124 may be provided over the sensation aspect 100. The three-dimensional film 124 may act as a trapping layer. Alternatively, as shown, a trapping layer 106 may be provided, over or under the film 124. Generally, the film 124 should not inhibit flow of the urine to the sensation aspect 100 but should reduce contact of the temperature sensation agent 102, for example sorbitol, with the body of the user. Suitable three-dimensional films are discussed in U.S. Pat. Nos. 3,929,135, 4,342,314, 4,463,045, and 5,137,537, all herein incorporated by reference.

Figure 16:
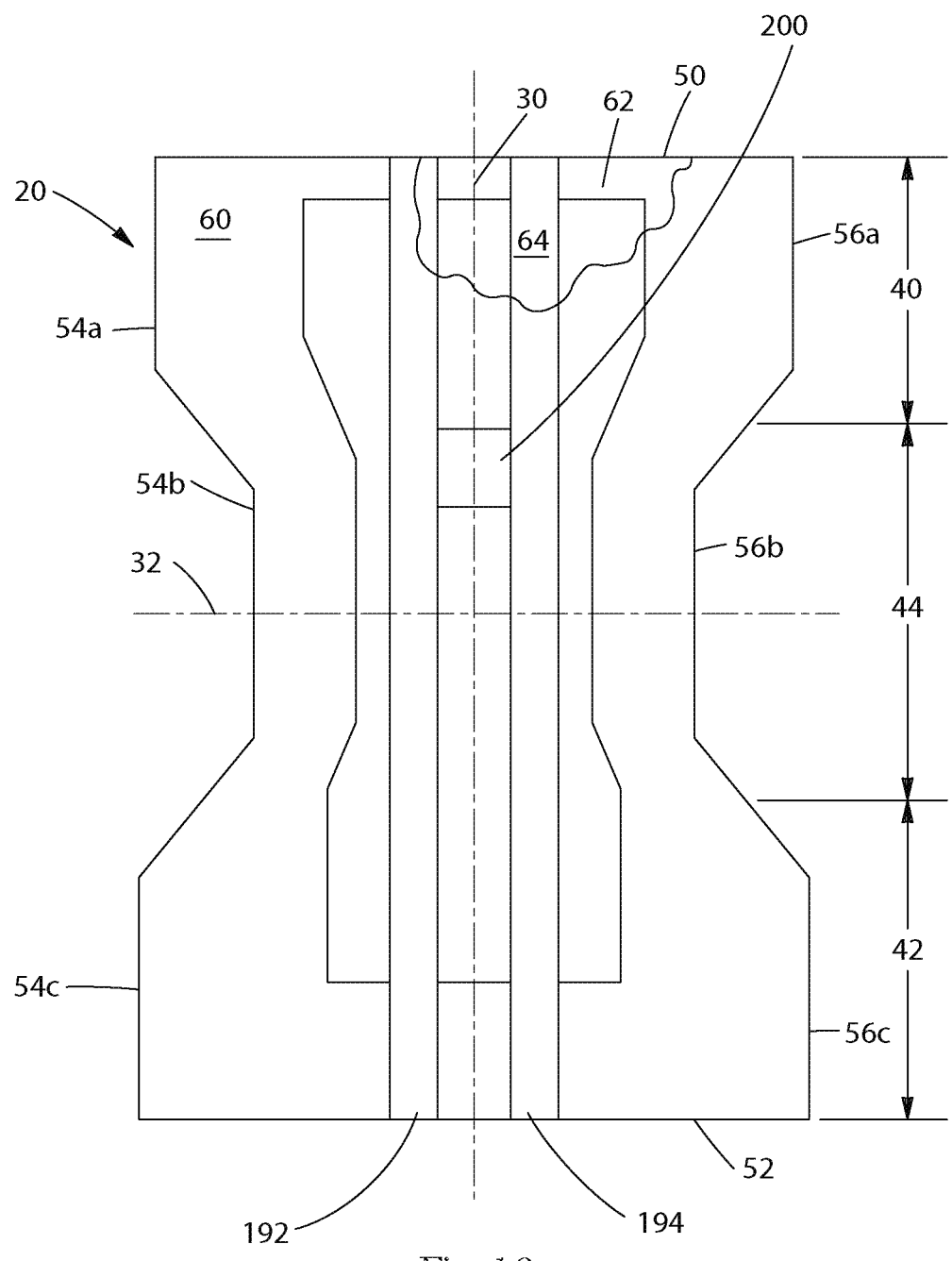
FIG. 16 illustrates a disposable absorbent article including a sensation aspect for wear by a boy in accordance with one embodiment of the present invention.
Figure 17:
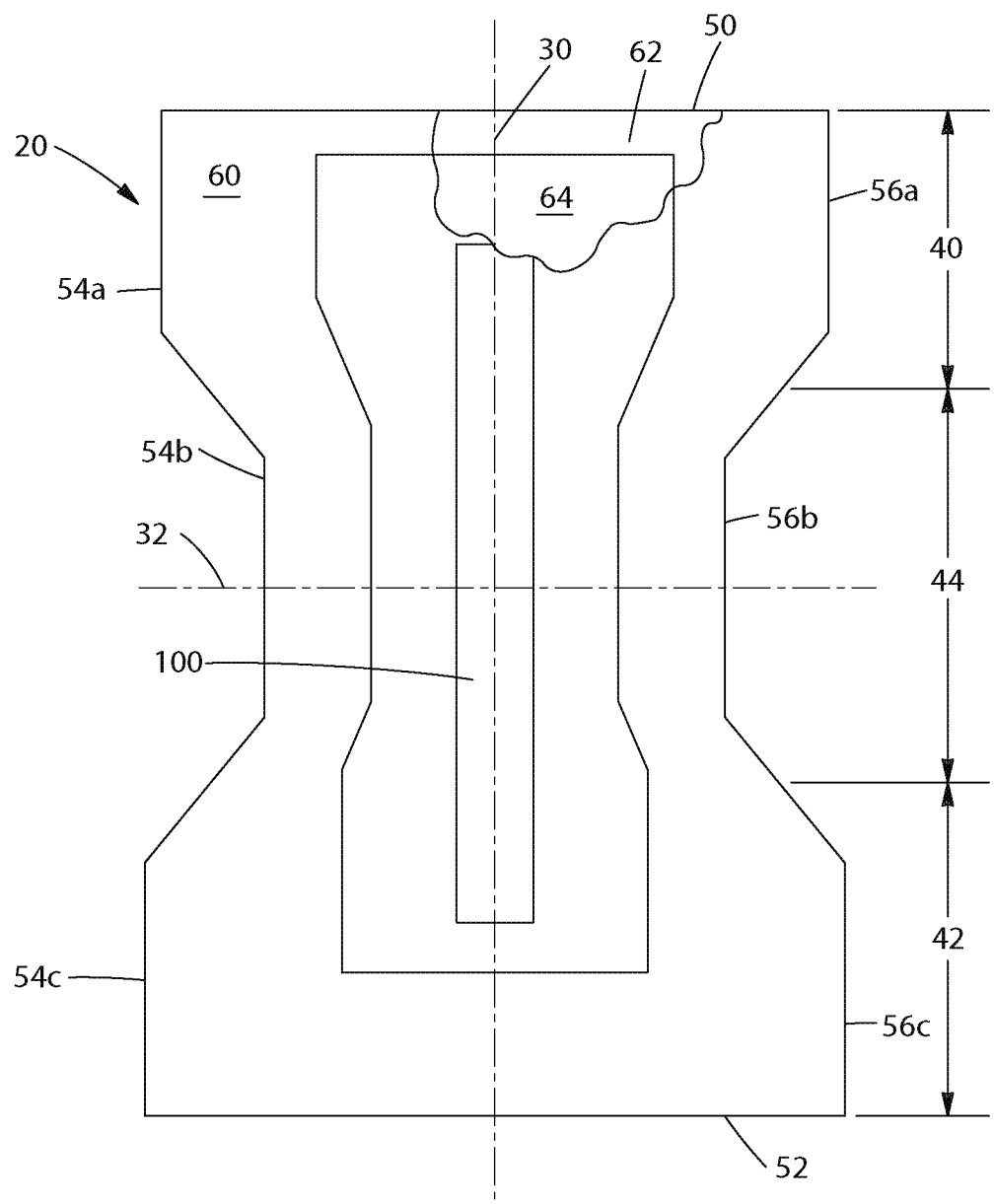
FIG. 17 illustrates a disposable absorbent article having a larger sensation aspect in accordance with one embodiment of the present invention.

As previously noted, in currently available diapers having a sensation aspect, the sensation aspect is of uniform size (approximately 3 inches by 3 inches) and placement (in the crotch area). FIGS. 16 and 17 illustrate embodiments having alternative sizing and placement of the sensation aspect. The sizing and placement of the sensation aspect may be varied according to gender, age of the wearer, and for additional usage.

Thus, in one embodiment, a smaller sensation aspect is provided for diapers designed for boys. Generally, boy genitalia has increased contact with the diaper than does girl genitalia. Accordingly, a greater amount of the sensation agent is necessary for providing a cooling sensation to a girl than to a boy. Further, the placement of the sensation aspect may be at a more forward position for a diaper for a boy and in lower position for a diaper for a girl, generally corresponding with the anticipated urination zone of the diaper. Thus, as shown in FIG. 16, the diaper 20 is designed for wear by a boy. The sensation aspect 100 thus is smaller and provided in a more forward position than that of FIG. 5.

Generally, diaper size increases with age. Thus, an older child uses a larger diaper. Correspondingly, as a very general matter, children further into toilet training typically are in larger diapers. Thus, the size and quantity of the sensation agent can by varied to increase or decrease the sensation generally or to increase or decrease the sensation corresponding to an amount of insult. Thus, for example, the size and quantity of the sensation agent may be varied with smaller diapers, for children just beginning toilet training, and larger diapers, for children closer to being toilet trained. For example, providing less temperature sensation agent will decrease the sensation emitted upon insult and providing more temperature sensation agent will increase the sensation emitted upon insult. FIG. 17 illustrates an embodiment of a diaper 20 having a larger sensation aspect 100 extending generally from the first waist region 40 to the second waist region 42 but in a narrower aspect.

In a first embodiment wherein the sensation aspect is varied according to size of diaper, the sensation aspect has a decreased quantity of agent with larger diapers. Thus, for example, a diaper 20 having a sensation aspect 100 generally sized such as that in FIG. 5 may be used for an older child closer to being toilet trained. Correspondingly, a diaper 20 having a sensation aspect 100 generally sized such as that in FIG. 17 may be used for a younger child beginning toilet training. Generally, children who are closer to being toilet trained are more sensitive to soiling of the diaper. Thus, it may not be necessary to provide as dramatic of an indicator of soiling of the diaper.

In a second embodiment wherein the sensation aspect is varied according to size of diaper, the sensation aspect has an increased quantity of agent and will emit increased sensation upon insult with larger diapers. Thus, for example, a diaper 20 having a sensation aspect 100 generally sized such as that in FIG. 17 may be used for an older child closer to being toilet trained. Correspondingly, a diaper 20 having a sensation aspect 100 generally sized such as that in FIG. 5 may be used for a younger child beginning toilet training. In some situations, a child may become desensitized to the cooling sensation of the sensation aspect after he or she has been using diapers with a sensation aspect for a longer period of time. Thus, it may be desirable to increase the agent.

Returning to FIG. 16, a diaper is shown including a sensation aspect 200. Elasticizing elements 192, 194 are provided proximate edges of the sensation aspect 200 extending over a larger portion of the diaper 20. The elasticizing elements 192, 194 elasticize the sensation aspect 200, which may assist in bringing the sensation aspect 20 in to close contact with the skin of the wearer. As shown, the first and second sides 192, 194 are arranged generally parallel to the longitudinal axis 30 of the article 20. As described above, with respect to the sensation aspect 100, the sensation aspect 200 may include an active component, such as (i) a coating, which may be a hydrophilic coating or a hydrophobic coating, (ii) a temperature sensation agent, which may in substitution for, in conjunction with, or combined with the coating, (iii) a layer of hydrophilic material, and/or (iv) a topsheet material.

Figure 18:
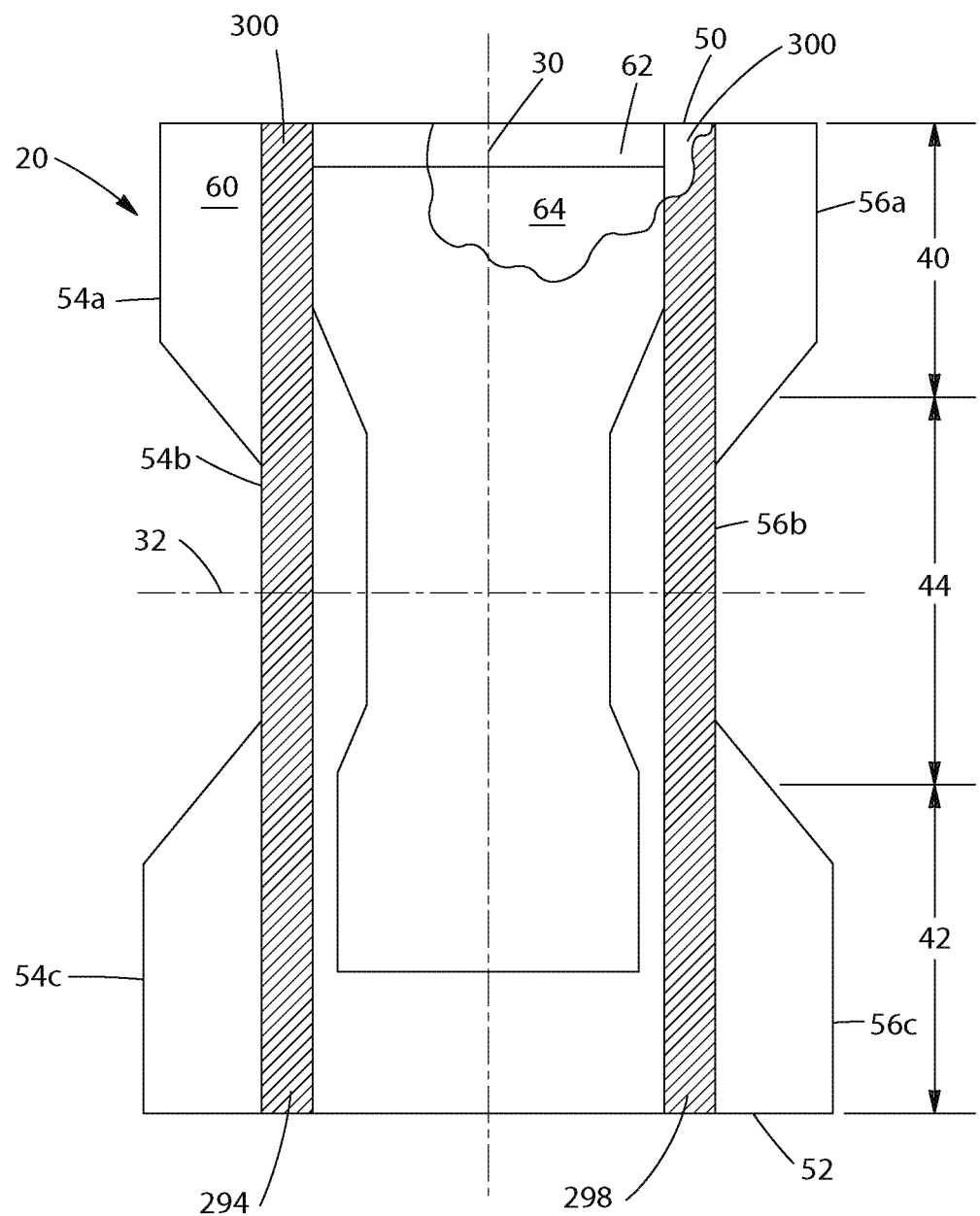
FIG. 18 illustrates a disposable absorbent article having a sensation aspect in a barrier cuff in accordance with another embodiment of the present invention.
Figure 19:
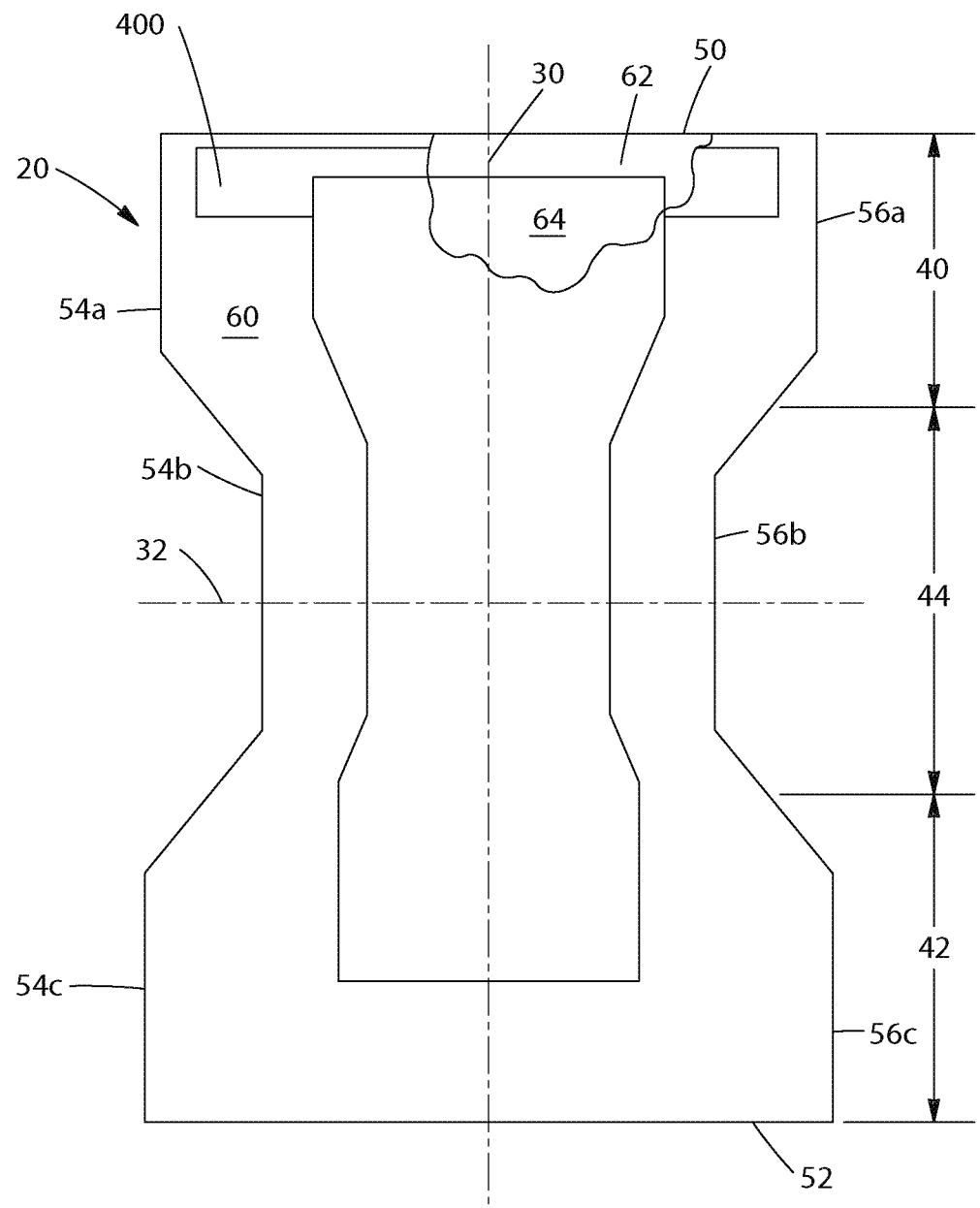
FIG. 19 illustrates a disposable absorbent article having a sensation aspect in a waist band in accordance with another embodiment of the present invention.

FIGS. 18 and 19 illustrate embodiments wherein the sensation aspect is provided at a location other than the crotch region. This location may be used as an alternative to or in addition to locating a sensation aspect in the crotch region.

As shown in FIG. 18, a sensation aspect 300 may be provided along the barrier cuffs 294, 298 of the diaper 20. The barrier cuff 294, 298 generally is the area along the legs of the wearer that prevents leakage through the sides of the diaper 20. The barrier cuff 294, 298 is typically directly adjacent the skin and, thus, has optimal contact for conveying a cooling sensation. The barrier cuff 294, 298 comprises an elastic cuff and an inner cuff. In the embodiment shown, the sensation aspect is provided with the inner cuff. The sensation aspect comprises a generally long, slender aspect having a temperature sensation agent. Layers of the barrier cuff 294, 298 are wrapped around the sensation aspect 300. The sensation aspect 300 may extend through the entire length of the barrier cuff 294, 298 or through only a portion thereof. The portion of the barrier cuff 294, 298 comprising the sensation aspect 300 should be chosen with consideration of contact with the wearer.

FIG. 19 illustrates an embodiment wherein a sensation aspect is provided along the waistband. The waistband is directly adjacent the skin and thus provides optimal contact for conveying a cooling sensation. Further, a caregiver can easily contact the waistband to determine if the sensation aspect has been activated. Generally, urine does not come into contact with the waistband. Thus, in embodiments wherein a sensation aspect is provided at the waistband, the urine must be wicked to the sensation aspect via, for example, an acquisition layer. As shown, the sensation aspect 400 is provided at the waist band along the laterally extending first waist edge 50 in the first waist region 40. Alternatively, or additionally, the sensation aspect 400 may be provided at the waist band along the laterally extending second waist edge 52 in the second waist region 42. The sensation aspect 400 is provided intermediate the core 64 and the topsheet 60. An acquisition layer is provided between the sensation aspect 400 and the topsheet 60, beginning at least around an area that normally comes into contact with urine, such as the crotch region 44, and extending to the waist region 40 housing the sensation aspect 400. Thus, urine is wicked from the area normally coming into contact with urine, such as the crotch region 44, to the sensation aspect 400.

Generally, the acquisition layer may be designed to wick urine to any location on the diaper. Thus, a sensation aspect may be provided at any suitable location on the diaper for communicating an alarm sensation to the wearer or to a caregiver. The location may be chosen to maximize skin contact with the wearer, discomfort for the wearer, accessibility for the caregiver, or based on other criteria.

Figure 20:
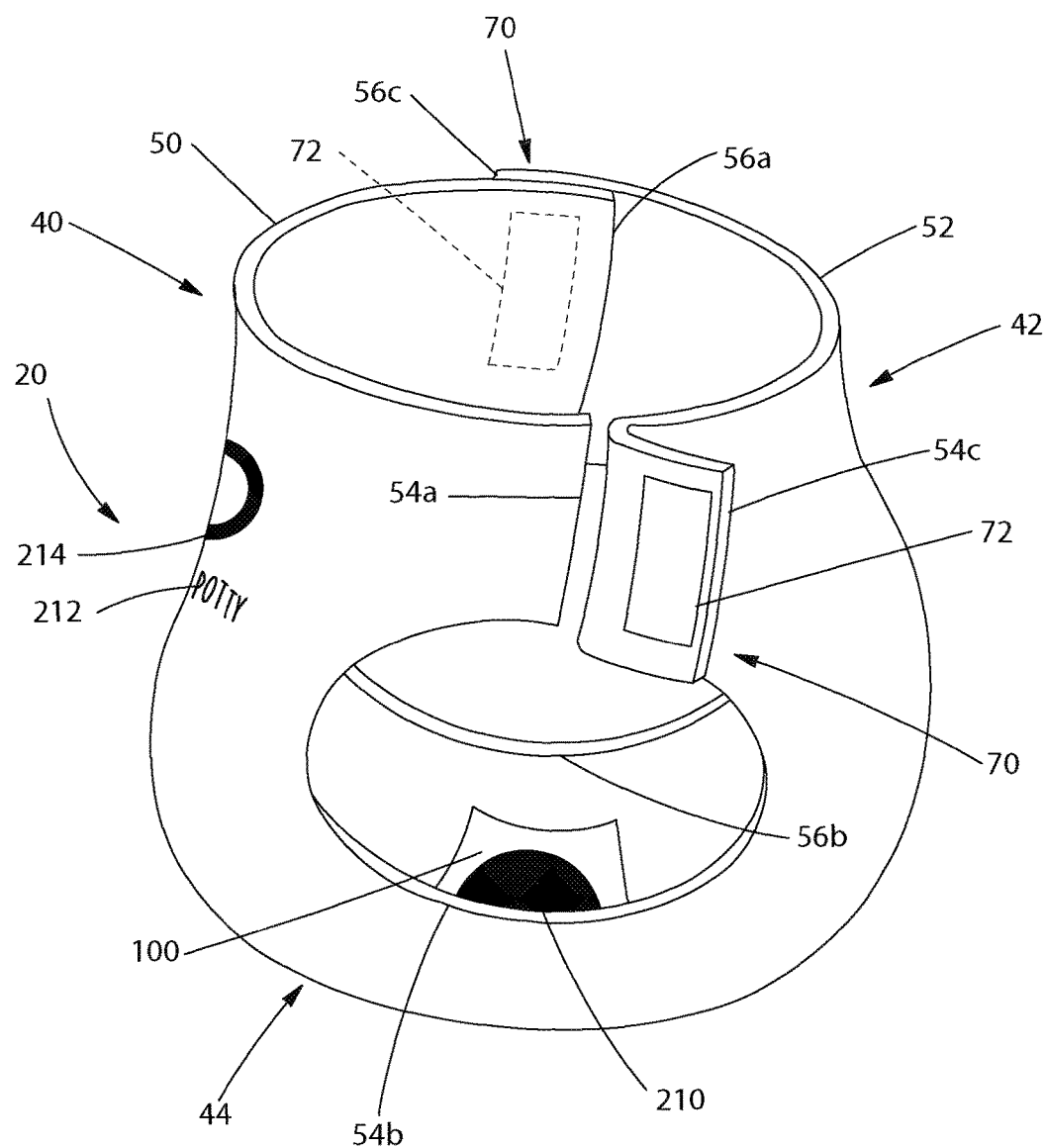
FIG. 20 illustrates a disposable absorbent article having a sensation aspect, an internal graphic, a first external graphic, and a second external graphic in accordance with one embodiment of the present invention.
Figure 21:
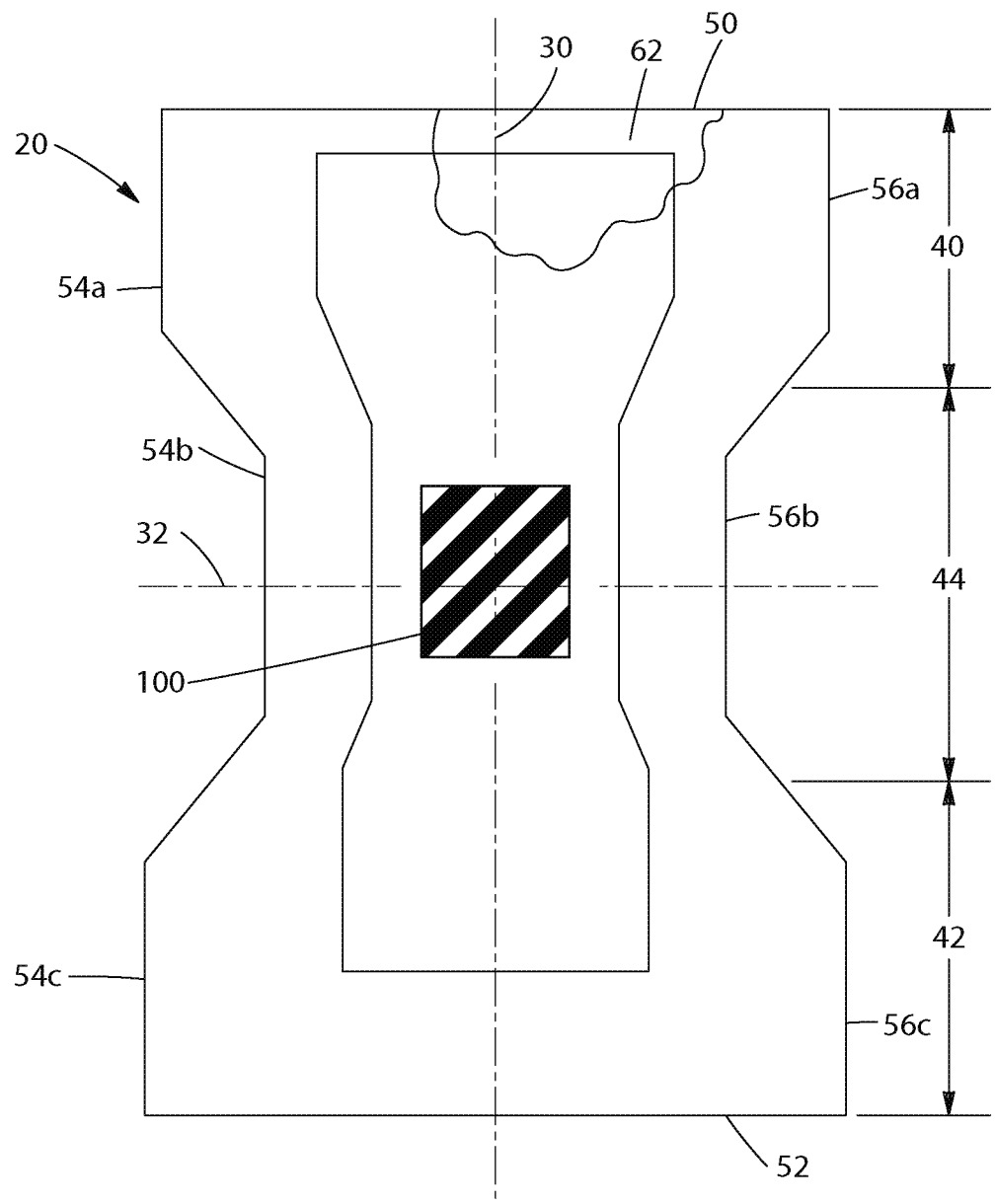
FIG. 21 illustrates a disposable absorbent article having a colored or graphically designed sensation aspect in accordance with one embodiment of the present invention.
Figure 22:
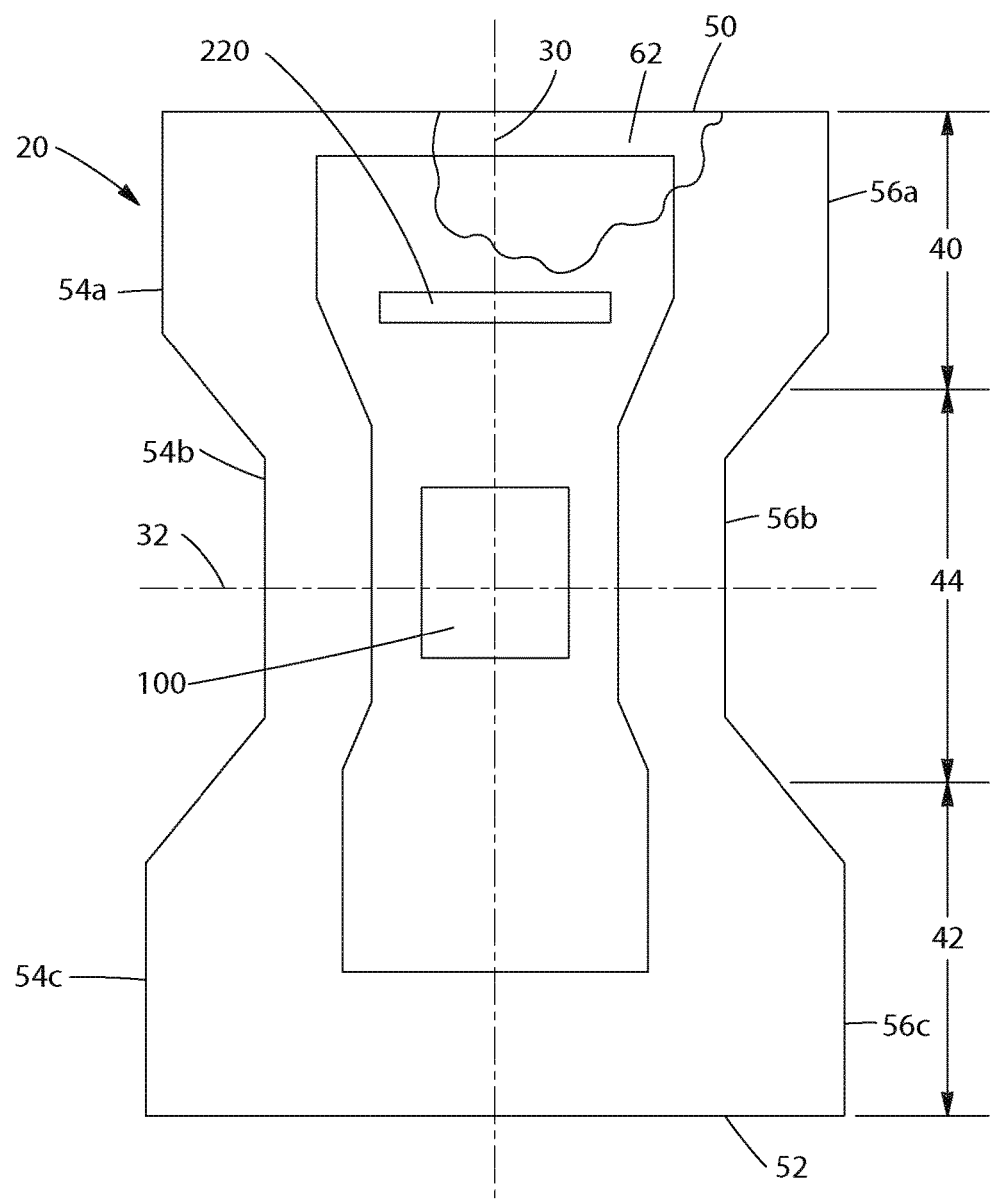
FIG. 22 illustrates a disposable absorbent article having a sensation aspect and a graphic, wherein the graphic is triggered by the activation of the sensation aspect, in accordance with one embodiment of the present invention.

FIGS. 20-22 illustrate embodiments of diapers having a sensation aspect wherein the diapers further include graphic indicators.

The disposable absorbent article 20 may have visible highlighting in the interior of the article and/or associated with the sensation aspect or members 100 to indicate the presence of the sensation aspect or members 100 and thereby facilitate an opportunity for the urinary toilet training of the wearer of the article. Such visible highlighting is described in U.S. Published Application No. 2005/0096612. Although a sensation aspect lacking this visible highlighting is fully functional in terms of providing a noticeable wetness and/or temperature signal to the wearer, the caregiver might overlook or forget the possibility of capitalizing on each opportunity for urinary toilet training if the body-facing portion of the absorbent article presents a generally uniform appearance, such as in absorbent articles that present a generally uniform white appearance on their body-facing surfaces.

Furthermore, once the caregiver decides to mention urinary toilet training to the wearer, the visible highlighting can serve to draw the wearer's interest or can be pointed out by the caregiver and incorporated into an explanation of the upcoming opportunity. Thus, the visible highlighting can provide a topic for conversation between the caregiver and the wearer on the subject of urinary toilet training and can likewise provide a nameable object for reference by the wearer, greatly simplifying the mental task required of the wearer who desires to communicate his or her need to go to the toilet or to communicate his or her improving recognition of the wetness signal provided by the sensation aspect.

Even a simple solid coloring form of visible highlighting can serve to facilitate an opportunity for urinary toilet training, especially when used with wearers possessing some recognition of colors or colored forms. In addition, visible highlighting in the form of a color or colors may facilitate the teaching of recognition of colors and differences between colors, and the associated learning may enhance the urinary toilet training process in turn.

In embodiments where the sensation aspect 100 is centrally located, for example in the crotch region 44, visible highlighting of the sensation aspect 100 may provide additional benefits related to the learning achieved by the wearer. For example, a visibly highlighted sensation aspect may provide a line of reference for the visual separation of the two leg openings, including their differentiation into right and left leg openings for the respective feet to be inserted into the corresponding leg openings. Similarly, a longitudinally oriented visible highlighting may serve as a visual reference for the front to back direction, both for orienting the article prior to applying it, if done by the caregiver, or prior to donning it, if done by the wearer. This longitudinally oriented visual reference may also aid in the teaching of such skills as wiping one's self clean after using the toilet by using a longitudinal motion. The concept of something being central or "in the middle" may be taught and learned by visual reference to the visible highlighting and this concept may then be applied to related subjects, such as the anatomical location of the source of urine and the corresponding proper position in which to sit on the toilet. Thus, in the above and similar ways, the wearer can be made more aware of his or her own body, which may tend to enhance and facilitate the urinary toilet training experience.

In addition, the visible highlighting can serve to enhance the self-esteem of the wearer through a reminder that he or she is mature enough to be engaged in urinary toilet training. This effect can be compounded when the wearer succeeds in recognizing the need to go to the toilet and then sees the dry condition of the visibly highlighted sensation aspect inside the article after pulling it down.

The visible highlighting may be provided by means of printing onto a surface of the sensation aspect 100 or one of its layers. For example, solid coloring or a graphic may be printed onto a trapping layer 106 or along the layer housing the temperature sensation agent 102. As another example, an adhesive or a gel may be printed onto a surface of either of the two layers. Such an adhesive or gel may be colored differently from the surrounding area. Alternatively, the adhesive or gel may be uncolored or may have the same color as the surrounding area, but may still provide visible highlighting by forming a distinctive raised area or pattern and/or by surrounding a distinctive recessed area or pattern. It is to be understood that the visible highlighting of the sensation aspect 100 when provided under the topsheet 60 should be sufficiently bright or colored to be seen through the topsheet 60.

The visible highlighting may also be provided by forming one or more layers of the sensation aspect of a colored material, for example, a fibrous layer containing colored fibers, a monolithic layer containing a dispersed or imbedded colorant, a layer of an unbleached material that is colored in its virgin state, and so on.

In some embodiments, the visible highlighting may be provided by impressing or embossing the sensation aspect or one of it layers. The impressed, embossed, or bonded portions of the sensation aspect may provide a tactile sensation in addition to visibly highlighting the presence and location of the sensation aspect. For instance, a raised area or a recessed area or the combination of raised and recessed areas adjacent to each other may be felt by the hand and, in some embodiments, may be felt by the wearer while wearing the article. Similarly, the raised area or pattern formed by a printed adhesive or gel, as mentioned above, may provide such a tactile sensation. Just as with the visible highlighting alone, the combination of visible highlighting and this tactile sensation can serve to draw the wearer's interest or can be pointed out by the caregiver and incorporated into an explanation of the upcoming opportunity for urinary toilet training.

In addition, the visible highlighting may be provided by incorporating distinctive fibers or filaments in one or both layers of the sensation aspect or by distinctively orienting fibers or filaments in one of these layers. For example, a fiber or a filament of a distinctive color may be incorporated into the coating to visibly highlight its presence and its location in the article. Similarly, a distinctively thicker fiber or filament may be embedded in one of the two layers and thereby a distinctive raised area or pattern.

If the portions of the structure of the absorbent article surrounding the sensation aspect are of one color, the visible highlighting can be provided by the use of another color, by the use of contrast, by the use of a different pattern in the same or a similar color, or by any other method that visibly differentiates the sensation aspect from the surrounding structural elements.

In some embodiments, the visible highlighting may include more than one color, more than one difference in contrast, more than one pattern, more than one graphic, more than one area of solid coloring, and so on, such that all portions of this description referring to the singular of a form of visible highlighting are meant to include the plural, and vice versa.

The visible highlighting may include open or closed geometric figures, a two dimensional representation of a three dimensional object, a representation of a commonly named or nameable shape or object, a representation of a recognizable object used in play, and/or a representation of a character that may be known to the wearer, such as a teddy bear, a character appearing on a television show for children, a character appearing in a game or a storybook for children, etc. In embodiments in which the visible highlighting includes a variety of figures, objects, and/or characters, the various elements of the visible highlighting may be interactively interrelated, related by subject matter, and/or related by a common story line. Conversely, the various elements may be interactively unrelated, unrelated by subject matter, and/or not related by a common story line.

When solid coloring is used, it may partially or completely fill the area bounded by a graphic outline, appear as shading inside or outside such a graphic outline, itself form a "filled-in" graphic, or simply uninterruptedly occupy an area, e.g., occupy the entire width of a layer of the sensation aspect over all or a portion of the corresponding length.

In some embodiments, the visible highlighting may become more or less visible when the sensation aspect is wetted. In addition, the visible highlighting may change color when the sensation aspect is wetted. Any of these effects may be created by the use of inks or dyes or other agents that undergo chemical reactions or are dispersed or concentrated when wetted by urine. In general, any of the wetness indicating compositions commonly used in externally visible wetness indicators, such as so-called "appearing" or "disappearing" wetness indicators that may become more or less visible when wetted and in wetness indicators that may change color when wetted, may be used for these versions of visible highlighting.

Rather than being structurally disposed in such a way as to provide a wetness indication that is visible from the outside of the absorbent article, according to at least one embodiment, any wetness indicating compositions used for the visible highlighting of the sensation aspect may be visible from the body-facing surface of the absorbent article. This different disposition enables the caregiver to apply different techniques to the task of urinary toilet training when using an absorbent article of the present disclosure, as compared to using an absorbent article having only a wetness indicator visible from the outside of the article. For example, while the change in an exterior wetness indicator is visible for all to see, any change in the visible highlighting of an interior sensation aspect remains "private" until either the caregiver or the wearer peers into the absorbent article or it is removed. Therefore, whether or not any wetting of the absorbent article has occurred can, itself, become the focus of a playful activity resembling a game, with the "secret" being revealed only when the caregiver and the wearer agree to conclude the game. If the wearer notices a sensation of wetness or merely desires to check the condition of the "private" indication, he or she can simply look inside the absorbent article. If the appearance of the visible highlighting has changed, the wearer can then choose to bring this to the attention of the caregiver in the context of asking to go to the bathroom. In addition, because the visible highlighting serves as a "private" indication, the wearer might be able to detect a change in its appearance before the appearance of any externally visible wetness indicator changes and thereby be the first person to mention the subject of going to the toilet. Furthermore, the provision of both visual and tactile sensations to the wearer may serve to reinforce the tactile sensation of wetness and thereby enhance the training effect of the sensation aspect. An absorbent article in which the wetting is indicated by both a sensation and a visible change in the appearance of the visible highlighting may thus facilitate faster learning on the part of the wearer.

Although the appearance of the visible highlighting remains "private" until either the caregiver or the wearer peers into the absorbent article or it is removed, the visible highlighting may be associatively correlated in visible form with marking that is located elsewhere in or on the absorbent article and is visible from the outside of the absorbent article. This externally visible marking may be permanent or may change in appearance while the absorbent article is being worn. For example, the externally visible marking may be an externally visible wetness indicator. By giving the visible highlighting of the sensation aspect a visible form that is similar to the visible form of an externally visible marking, an opportunity for urinary toilet training may be enhanced. For instance, the caregiver can point out the similarity between the externally visible marking and the "private" visible highlighting of the sensation aspect and ask the wearer to remember the hidden visible highlighting every time he or she notices the externally visible marking.

Thus, for example, as shown in FIG. 20, the article 20 may comprise an internal graphic or coloring 210 on the sensation aspect 100 visible through the topsheet, a first external graphic 212, and a second external graphic 214. Any of the graphics 210, 212, or 214 may be permanent or may be "appearing or disappearing." With particular reference to the internal graphic 212, when permanent, the internal graphic may further darken when wettened, thus providing a visible indicator to the wearer of urination, as described above. In the embodiment shown, the internal graphic 210 is a solid circle. In FIG. 20, the topsheet is not illustrated to better illustrate the sensation aspect 100 and associated internal graphic 210. It should be appreciated that the topsheet would be provided over the sensation aspect 100. The first external graphics 212 may include a character image resembling a boy and a text graphic including words forming a message, such as "Remember to go to the potty!" While the graphics may include text, the primary form of communication may be symbols, icons, or other markings other than words, so that a pre-literate child may comprehend and follow the instructions or other information indicated by the graphics, although it is not necessary for the images to be understood at this level. The second external graphics 214 may include an image that may be associatively correlated to the permanent graphic, such as a ring. The second external graphics 214, when correlative to the internal graphic 210, may be appearing such that it appears when the internal graphic 210 has been wettened, thus providing an external indicator of urination.

Variations regarding the internal/external graphics are possible. For example, a permanent external image may be combined with the first and second external graphics, or only one external graphic may be included. Furthermore, character images other than a boy may be provided, such as a girl, an animal (which may be anthropomorphic), a cartoon character, and the like. Still further, additional or alternative text may be provided. Additionally exemplary graphics, graphics characteristics and/or arrangements (e.g., timings, themes, scenes, storylines, etc.), the materials that are suitable for forming the graphics, and the arrangement and/or joining of these materials to the article 20 are described in co-pending and commonly assigned U.S. patent application Ser. No. 11/098,362, filed in the name of Roe et al. on Apr. 4, 2005.

Even in embodiments in which the appearance of the visible highlighting is not affected by its being wetted, the associative correlation of the respective visible forms of an externally visible marking and the visible highlighting may serve to facilitate an opportunity for urinary toilet training. For example, if both the externally visible marking and the visible highlighting have the visible form of similar graphics, the externally visible marking can serve to draw the wearer's interest or can be pointed out by the caregiver and incorporated into an explanation of the ongoing opportunity for urinary toilet training.

Such associative correlation of the respective visible forms of an externally visible marking and the visible highlighting can be achieved without the respective visible forms being similar, so long as the respective visible forms are mutually related in a recognizable way. For example, the visible forms may be related in subject matter and/or may be related by a common story line and/or be interactively interrelated. Even an associative correlation of a simple solid coloring form of an externally visible marking with a similar solid coloring form of visible highlighting can serve to facilitate an opportunity for urinary toilet training, especially when used with wearers possessing some recognition of colors or colored forms.

Alternatively, the visible highlighting may be associatively uncorrelated with any externally visible marking. The lack of associative correlation may be complete or may be specific, e.g., the respective visible forms of the visible highlighting and the externally visible marking may be unrelated in subject matter, not related by a common story line, and/or interactively unrelated, while still being associatively correlated in another way.

The visible form of the visible highlighting of the sensation aspect need not be associatively correlated with the concept of urinary toilet training. However, in some embodiments, the visible form of the visible highlighting may be associatively correlated with the concept of urinary toilet training by, for example, providing a visual reference to the liquid-related nature of urinary toilet training, such as wetness, dryness, protection from wetness, the flow of a liquid, water, et cetera, and thus may serve to facilitate an opportunity for urinary toilet training.

The visible highlighting may emphasize dryness by depicting the sun, fair weather clouds, a sunny day, etc., while wetness may be referenced by a depiction of a water puddle, a cloud with falling rain, etc. A visual reference to protection from wetness may be provided by a depiction of an umbrella, a raincoat, a rain hat, galoshes, a submarine, or some other object that may be associated by the wearer with the concept of staying dry in a wet environment.

In any of these visible forms of visible highlighting that are associatively correlated with the concept of urinary toilet training, a human form and/or a recognizable character may be depicted in the visible highlighting. For example, a child may be shown in conjunction with inanimate objects, a child may be shown sitting on a potty chair, and/or a character from a children's storybook or a children's television program may be shown in similar poses, etc.

In current diapers having a sensation aspect, the sensation aspect may not be visible to an observer, either before or after soiling. As described above, visible indication of the sensation aspect, either when dry or wet or both, can have value through its training benefits. Providing a visible indication of the positioning of the sensation aspect provides positive teaching opportunities. FIG. 21 illustrates the sensation aspect 100 having a color or design associated therewith to indicate the placement of the sensation aspect 100 and/or soiling of the sensation aspect 100. In embodiments wherein the sensation aspect 100 is provided beneath a topsheet, the color or design of the sensation aspect 100 should be visible through the topsheet. This may be achieved via choice of color or design and/or modification of the topsheet. Providing a color or design on the sensation aspect 100 provides clarity regarding the source of the sensation and identifies the target zone. The design may be provided by a pattern printed on the sensation aspect 100. Alternatively, the sensation aspect 100 may be colored by coloring the temperature sensation agent within the sensation aspect 100. Thus, for example, if the temperature sensation agent is sorbitol, the sorbitol may be colored, thus providing color to the sensation aspect 100. In a first embodiment corresponding to a colored temperature sensation agent, the temperature sensation agent may be essentially without color when dry and colored when wet. Alternatively, the temperature sensation agent may be colored when dry but have a darker color after soiling. Thus, visual indication is given of the insult—thus informing a caregiver that the diaper has been soiled. In a further embodiment corresponding to a colored temperature sensation agent, the temperature sensation may have the same level of color in both dry and wet states. Thus, visual indication of the placement of the sensation aspect is provided.

In the embodiment of FIG. 23, a graphic signal 220 is triggered by the sensation. Thus, urine triggers the sensation aspect 100 to emit a sensation. The emitted sensation then triggers a graphic signal 220. The graphic signal 220 may be referred to as an active graphic and may be provided on either or both of the interior of the disposable absorbent article 20 or the exterior of the disposable absorbent article 20. Such graphic signal 220 may provide further information to a caregiver. For example, the graphic signal 220 may indicate the number of insults (or amount of times urinated upon), the change in temperature (indicating the amount of temperature sensation), or other. The graphic signal 220 may be visible from either the interior of the diaper 20 or from the exterior of the diaper 20. The sensation aspect 100 thus emits a tactile sensation when contacted urine. The tactile sensation in turn activates a non-tactile signal from the graphic signal 220. The non-tactile signal may comprise enhancement of or fading of a color or design. Thus, in one embodiment, the non-tactile signal comprises the graphic signal 220 becoming faint in response to the sensation emitted by the sensation aspect 100. In another embodiment, the non-tactile signal comprises the graphic signal 220 changing from a relatively faint appearance to a more bold appearance in response to the sensation emitted by the sensation aspect 100. In yet another embodiment, the non-tactile signal comprises the graphic signal 220 becoming visible in response to the sensation emitted by the sensation aspect 100. And in yet a further embodiment, the non-tactile signal comprises the graphic signal 220 changing colors in response to the sensation emitted by the sensation aspect 100. Any suitable means of communicating the sensation from the sensation aspect 100 to the graphic signal 220 may be used.

In further embodiments, the active graphic signal 220 may be designed to give more information to caregiver. For example, the graphic signal 220 may indicate the number of insults, the temperature drop, or other.

Although the invention has been described with reference to preferred embodiments, persons skilled in the art will recognize that changes may be made in form and detail without departing from the spirit and scope of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a backsheet;
   a topsheet having a body-facing surface;
   an absorbent core disposed between the backsheet and the topsheet, wherein the absorbent core includes a targeted zone of reduced absorbent capacity that absorbs less urine than surrounding areas of the core; and a temperature sensation aspect that produces a change in temperature when wet, the sensation aspect including a carrier layer and a temperature sensation agent, the temperature sensation aspect being provided between the core and the topsheet; and wherein the temperature sensation aspect is positioned on the targeted zone of reduced absorbent capacity on the core that correlates to a sensation aspect position of the core.

2. The absorbent article of claim 1, wherein the temperature sensation agent is sorbitol.

3. The absorbent article of claim 2, further comprising a three-dimensional film provided over the temperature sensation agent, the three-dimensional film being suited for reducing contact of the temperature sensation agent with skin.

4. The absorbent article of claim 1, further comprising an acquisition layer between the absorbent core and the sensation aspect, wherein the acquisition layer wicks urine from the sensation aspect position of the core.

5. The absorbent article of claim 1, wherein the sensation aspect comprises folds.

6. An absorbent article comprising:
a backsheet;
a topsheet having a body-facing surface;
an absorbent core disposed between the backsheet and the topsheet; and
a temperature sensation aspect that produces a change in temperature when wet, the temperature sensation aspect including a carrier layer and a temperature sensation agent, the temperature sensation aspect being provided between the core and the topsheet; wherein the temperature sensation aspect includes travel paths for urine flow wherein the travel paths comprise holes in the carrier layer for increased urine flow therethrough.

7. The absorbent article of claim 6, wherein the temperature sensation agent is sorbitol.

8. The absorbent article of claim 6, further comprising a three-dimensional film provided over the temperature sensation agent, the three-dimensional film being suited for reducing contact of the temperature sensation agent with skin.

9. The absorbent article of claim 6, wherein the temperature sensation agent is provided in concentrated areas on the sensation aspect.

10. The absorbent article of claim 6, wherein the carrier layer is hydrophilic.

11. An absorbent article comprising:
a backsheet;
a topsheet having a body-facing surface;
an absorbent core disposed between the backsheet and the topsheet, wherein the absorbent core includes a targeted zone of reduced absorbent capacity that absorbs less urine than surrounding areas of the core; and
a temperature sensation aspect that produces a change in temperature when wet, the temperature sensation aspect including a carrier layer and a temperature sensation agent, the temperature sensation aspect being provided between the core and the topsheet; wherein the temperature sensation aspect includes a graphic indicator for indicating placement or action of the sensation aspect; and
wherein the targeted zone of reduced absorbent capacity of the absorbent core is adjacent the temperature sensation aspect.

12. The absorbent article of claim 11, wherein the sensation aspect has a color contrasting with a color of the absorbent article.

13. The absorbent article of claim 12, wherein the color of the sensation aspect darkens when wet.

14. The absorbent article of claim 11, wherein the graphic indicator appears when the sensation aspect becomes wet.

15. The absorbent article of claim 11, further comprising an active graphic, the active graphic being triggered by activation of the sensation aspect.

16. The absorbent article of claim 15, wherein the active graphic is provided on at least an exterior of the absorbent article.

17. The absorbent article of claim 15, wherein the active graphic is provided on at least an interior of the absorbent article.

18. The absorbent article of claim 15, the sensation aspect comprising a temperature sensation agent, wherein the graphic indicator is provided by coloring the sensation agent.

* * * * *